(12) United States Patent
Tavtigian et al.

(10) Patent No.: US 6,440,699 B1
(45) Date of Patent: Aug. 27, 2002

(54) PROSTATE CANCER SUSCEPTIBLE CA7 CG04 GENE

(75) Inventors: Sean V. Tavtigian; Brad Swedlund, both of Salt Lake City, UT (US); Jacques Simard, Maures; Johanna M. Rommens, Toronto, both of (CA)

(73) Assignees: Myriad Genetics, Inc., Salt Lake City, UT (US); Hospital for Sick Children, The, Toronto, Ontario (CA)

( * ) Notice: Subject to any disclaimer, the term of this patent is extended or adjusted under 35 U.S.C. 154(b) by 0 days.

(21) Appl. No.: 09/568,816

(22) Filed: May 11, 2000

Related U.S. Application Data
(60) Provisional application No. 60/134,209, filed on May 14, 1999.

(51) Int. Cl.⁷ .................................................. C12P 21/06
(52) U.S. Cl. ................... 435/69.1; 435/320.1; 435/325; 536/23.1; 536/23.5
(58) Field of Search ............................. 536/23.1, 23.5; 435/320.1, 69.1, 325; 424/93.2; 530/350

(56) References Cited

PUBLICATIONS

Ngo et al., Computational complexity, protein structure predition, and the levinthal paradox, 1994, The Protein Folding Problem and Tertiary Structure Prediction, pp. 491–494.*

Chiu et al., Optimizing energy potentilas for success in protein tertiary structure, 1998, Folding & Design, vol. 3, pp. 223–228.*

Mountain, Gene therapy: the first decade, 2000, Tibtech, vol. 18, pp. 119–128.*

Anderson, Human gene therapy, 1998, Nature, vol. 392, pp. 25–30.*

Verma et al, Gene therapy–promises, problems and prospects, 1997, Nature, vol. 389, pp. 239–242.*

* cited by examiner

Primary Examiner—Dave T. Nguyen
Assistant Examiner—Brian Whiteman
(74) Attorney, Agent, or Firm—Rothwell, Figg, Ernst & Manbeck

(57) ABSTRACT

A human gene which is here named CA7 CG04 has been identified in which mutations have been found which have been correlated with prostate cancer.

18 Claims, No Drawings

PROSTATE CANCER SUSCEPTIBLE CA7 CG04 GENE

CROSS-REFERENCE TO RELATED APPLICATION

The present application is related to provisional patent application Serial No. 60/134,209 filed on May 14, 1999, incorporated herein by reference.

FIELD OF THE INVENTION

The present invention relates generally to the field of human genetics. Specifically, the present invention relates to methods and materials used to isolate and detect a human prostate cancer predisposing gene (identified as CA7 CG04 herein), some mutant alleles of which cause susceptibility to cancer, in particular, prostate cancer. More specifically, the invention relates to germline mutations in the CA7 CG04 gene and their use in the diagnosis of predisposition to prostate cancer. The present invention further relates to somatic mutations in the CA7 CG04 gene in human prostate cancer and their use in the diagnosis of human prostate cancer. Additionally, the invention relates to somatic mutations in the CA7 CG04 gene in other human cancers and their use in the diagnosis and prognosis of human cancers. The invention also relates to the therapy of human cancers which have a mutation in the CA7 CG04 gene. The invention further relates to the screening of drugs for cancer therapy. Finally, the invention relates to the screening of the CA7 CG04 gene for mutations, which are useful for diagnosing the predisposition to prostate cancer.

The publications and other materials used herein to illuminate the background of the invention, and in particular, cases to provide additional details respecting the practice, are incorporated herein by reference, and for convenience, are referenced by author and date in the following text and respectively grouped in the appended List of References.

BACKGROUND OF THE INVENTION

The genetics of cancer is complicated, involving gain or loss of function of three loosely defined classes of genes: (1) dominant, positive regulators of the transformed state (oncogenes); (2) recessive, negative regulators of the transformed state (tumor suppressor genes); (3) recessive genes involved in maintenance of genome integrity (caretaker genes) (Kinzler and Vogelstein, 1997). Over one hundred oncogenes have been characterized. About a dozen tumor suppressor and a similar number of caretaker genes have been identified; the number of genes falling into these last two classes is expected to increase beyond fifty (Knudson, 1993).

The involvement of so many genes underscores the complexity of the growth control mechanisms that operate in cells to maintain the integrity of normal tissue. This complexity is manifest in another way. So far, no single gene has been shown to participate in the development of all, or even the majority of, human cancers. The most common oncogenic mutations are in the H-ras gene, found in 10–15% of all solid tumors (Anderson et al., 1992). The most frequently mutated tumor predisposition genes are the TP53 gene, homozygously deleted or mutated in roughly 50% of all tumors, and CDKN2, which was homozygously deleted in 46% of tumor cell lines examined (Kamb et al., 1994). Without a target that is common to all transformed cells, the dream of a "magic bullet" that can destroy or revert cancer cells while leaving normal tissue unharmed is improbable.

The hope for a new generation of specifically targeted antitumor drugs may rest on the ability to identify oncogenes, tumor suppressor, and caretaker genes that play general roles in the process of oncogenesis.

Specific germline alleles of certain oncogenes, tumor suppressor, and caretaker genes are causally associated with predisposition to cancer. This set of genes is referred to as tumor predisposition genes. Some of the tumor predisposition genes which have been cloned and characterized influence susceptibility to: 1) Retinoblastoma (RB 1); 2) Wilms' tumor (WT1); 3) Li-Fraumeni (TP53); 4) Familial adenomatous polyposis (APC); 5) Neurofibromatosis type 1 S(NF1); 6) Neurofibromatosis type 2 (NF2); 7) von Hippel-Lindau syndrome (VHL); 8) Multiple endocrine neoplasia type 2A (MEN2A); 9) Melanoma (CDKN2 and CDK4); 10) Breast and ovarian cancer (BRCA1 and BRCA2); 11) Cowden disease (MMAC1); 12) Multiple endocrine neoplasia (MEN1); 13) Nevoid basal cell carcinoma syndrome (PTC); 14) Tuberous sclerosis 2 (TSC2); 15) Xeroderma pigmentosum (genes involved in nucleotide excision repair); 16) Hereditary nonpolyposis colorectal cancer (genes involved in mismatch repair).

Tumor predisposition loci that have been mapped genetically but not yet isolated include genes for: Lynch cancer family syndrome 2 (LCFS2); Neuroblastoma (NB); Beckwith-Wiedemann syndrome (BWS); Renal cell carcinoma (RCC); and Tuberous sclerosis 1 (TSC1). Tumor predisposition genes that have been characterized to date encode products with similarities to a variety of protein types, including DNA binding proteins (WT1), ancillary transcription regulators (RB1), GTPase activating proteins or GAPs (NF1), cytoskeletal components (NF2), membrane bound receptor kinases (MEN2A), cell cycle regulators (CDKN2 and CDK4), tyrosine phosphatases (MMAC 1), as well as others with no obvious similarity to proteins of known function (BRCA2).

In many cases, the tumor predisposition gene originally identified through genetic studies has been shown to be lost or mutated in some sporadic tumors. This result suggests that regions of chromosomal aberration, whether germline, in tumors, or in tumor cell lines, may signify the position of important tumor predisposition genes involved both in genetic predisposition to cancer and in sporadic cancer.

Prostate cancer is the most common cancer in men in many western countries, and the second leading cause of cancer deaths in men. It accounts for more than 40,000 deaths in the U.S. annually. The number of deaths is likely to continue rising over the next 10 to 15 years. In the U.S., prostate cancer is estimated to cost $1.5 billion per year in direct medical expenses. In addition to the burden of suffering, it is a major public-health issue. Numerous studies have provided evidence for familial clustering of prostate cancer, indicating that family history is a major risk factor for this disease (Cannon et al., 1982; Steinberg et al., 1990; Carter et al, 1993).

Prostate cancer has long been recognized to be, in part, a familial disease. Numerous investigators have examined the evidence for genetic inheritance and concluded that the data are most consistent with dominant inheritance for a major susceptibility locus or loci. Woolf (1960), described a relative risk of 3.0 of developing prostate cancer among first-degree relatives of prostate cancer cases in Utah using death certificate data. Relative risks ranging from 3 to 11 for first-degree relatives of prostate cancer cases have been reported (Cannon et al., 1982; Woolf, 1960; Fincham et al., 1990; Meikle et al., 1985; Krain, 1974; Morganti et al., 1956; Goldgar et al., 1994). Carter et al. (1992) performed segregation analysis on families ascertained through a single prostate cancer proband. The analysis suggested Mendelian inheritance in a subset of families through autosomal dominant inheritance of a rare (q=0.003), high-risk allele with estimated cumulative risk of prostate cancer for carriers of 88% by age 85. Inherited prostate cancer susceptibility accounted for a significant proportion of early-onset disease, and overall was responsible for 9% of prostate occurrence by age 85. Recent results demonstrate that at least two loci exist which convey susceptibility to prostate cancer as well as other cancers. These loci are HPC1 on chromosome lq, (Smith et al., 1996), HPCX on chromosome Xp (Xu et al., 1998), and one or more loci responsible for the unmapped residual.

Smith et al., (1996) indicated that the inherited prostate susceptibility in kindreds with early age onset is linked to chromosome 1 (the HPC1 locus or region). Most strategies for cloning a chromosome 1-linked prostate cancer predisposing gene require precise genetic localization studies. The simplest model for the functional role of a prostate cancer predisposing gene holds that alleles of prostate cancer predisposing gene that predispose to cancer are recessive to wild type alleles; that is, cells that contain at least one wild type allele are not cancerous. However, cells that contain one wild type allele and one predisposing allele may occasionally suffer loss of the wild type allele either by random mutation or by chromosome loss during cell division (nondisjunction). All the progeny of such a mutant cell lack the wild type function of the gene and may develop into tumors. According to this model, predisposing alleles of the gene are recessive, yet susceptibility to cancer is inherited in a dominant fashion: men who possess one predisposing allele (and one wild type allele) risk developing cancer, because their prostate cells may spontaneously lose the wild type allele. This model applies to both tumor suppressor and caretaker genes described above. By inference this model may also explain the HPC1 function, as has recently been suggested (Smith et al., 1996).

A second possibility is that prostate cancer predisposing alleles are truly dominant; that is, a wild type allele cannot overcome the tumor-forming role of the predisposing allele. Thus, a cell that carries both wild type and mutant alleles would not necessarily lose the wild type copy before giving rise to malignant cells. Instead, prostate cells in predisposed individuals would undergo some other stochastic change(s) leading to cancer.

If a prostate cancer predisposing alleles are recessive, the prostate cancer predisposing gene is expected to be expressed in normal prostate tissue but not functionally expressed in prostate tumors. In contrast, if prostate cancer predisposing alleles are dominant, the wild type gene may or may not be expressed in normal prostate tissue. However, the predisposing allele will likely be expressed in prostate tumor cells.

Evidence for a prostate cancer susceptibility locus (identified in the literature as HPC1) on the long arm of chromosome 1, which is hypothesized to explain approximately 35% of families, was recently presented (Smith et al., 1996). Although several groups report evidence supporting this localization, it has not yet been confirmed statistically. Both the original Smith et al. report and a subsequent analysis of additional families (Cooney et al., 1997), suggest that the bulk of linkage evidence comes from African-American high-risk kindreds. In addition, it appears that this gene predisposes (although not exclusively) primarily to early onset prostate cancer. The chromosome 1 linkage of HPC1 has not been statistically confirmed; however, a report by Cooney et al. (1997) as well as a report by Neuhausen et al. (1977) are suggestive of confirmation, with less-than-significant indications of linkage at the location suggested to harbor HPC1.

Identification of a prostate cancer predisposition locus would permit the early detection of susceptible individuals and greatly increase our ability to understand the initial steps which lead to cancer. Cloning prostate cancer genes would also be important in the development of better diagnostic and prognostic products, as well as better cancer therapies.

SUMMARY OF THE INVENTION

The present invention relates generally to the field of human genetics. Specifically, the present invention relates to methods and materials used to isolate and detect a human prostate cancer predisposing gene located within the HPC1 region (identified herein as the CA7 CG04 gene), some alleles of which cause susceptibility to cancer, in particular prostate cancer. For example, mutations in the CA7 CG04 gene have been found to segregate with prostate, breast, cervical and other cancers. More specifically, the present invention relates to germline mutations in the CA7 CG04 gene and their use in the diagnosis of predisposition to prostate cancer. The invention also relates to presymptomatic therapy of individuals who carry deleterious alleles of the CA7 CG04 gene. The invention further relates to somatic mutations in the CA7 CG04 gene in human prostate cancer and their use in the diagnosis and prognosis of human prostate cancer. Additionally, the invention relates to somatic mutations in the CA7 CG04 gene in other human cancers and their use in the diagnosis of human cancers. The invention also relates to the therapy of human cancers which have a mutation in the CA7 CG04 gene. The invention further relates to the screening of drugs for cancer therapy. Finally, the invention relates to the screening of the CA7 CG04 gene for mutations or for overexpression, which are useful for diagnosing the predisposition to prostate cancer.

DETAILED DESCRIPTION OF THE INVENTION

The present invention relates generally to the field of human genetics. Specifically, the present invention relates to methods and materials used to isolate and detect a human prostate cancer predisposing gene (identified herein as the CA7 CG04 gene), some alleles of which cause susceptibility to cancer, in particular prostate cancer. More specifically, the present invention relates to germline mutations in the CA7 CG04 gene and their use in the diagnosis of predisposition to prostate cancer. The invention also relates to presymptomatic therapy of individuals who carry deleterious alleles of the CA7 CG04 gene. The invention further relates to somatic mutations in the CA7 CG04 gene in human prostate cancer and their use in the diagnosis of human prostate cancer. Additionally, the invention relates to somatic mutations in the CA7 CG04 gene in other human cancers and their use in the diagnosis and prognosis of human cancers. The invention also relates to the therapy of human cancers which have a mutation in the CA7 CG04 gene. The invention further relates to the screening of drugs for cancer therapy. Finally, the invention relates to the screening of the CA7 CG04 gene for mutations or overexpression, which are useful for diagnosing the predisposition to prostate cancer.

The present invention provides an isolated polynucleotide comprising all, or a portion of the CA7 CG04 locus or of a mutated CA7 CG04 locus, preferably at least eight bases and not more than about 300 kb in length. Such polynucleotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the CA7 CG04 locus or its expression product in an analyte. Such methods may further comprise the step of amplifying the portion of the CA7 CG04 locus, and may further include a step of providing a set of polynucleotides which are primers for amplification of said portion of the CA7 CG04 locus. The method is useful for either diagnosis of the predisposition to cancer or the diagnosis or prognosis of cancer.

The present invention further provides an isolated polypeptide comprising all or part of the polypeptide encoded by the CA7 CG04 gene or a mutated form of the polypeptide. An analysis of the sequence of the CA7 CG04 polypeptide shows similarities with Guansoine Exchange Factor (GEF) proteins. Thus, the CA7 CG04 polypeptide is a GEF protein and functions as a ras activator.

The present invention also provides isolated antibodies, preferably monoclonal antibodies, which specifically bind to an isolated polypeptide comprised of at least five amino acid residues encoded by the CA7 CG04 locus.

The present invention also provides kits for detecting in an analyte a polynucleotide comprising a portion of the CA7 CG04 locus, the kits comprising a polynucleotide complementary to the portion of the CA7 CG04 locus packaged in a suitable container, and instructions for its use.

The present invention further provides methods of preparing a polynucleotide comprising polymerizing nucleotides to yield a sequence comprised of at least eight consecutive nucleotides of the CA7 CG04 locus; and methods of preparing a polypeptide comprising polymerizing amino acids to yield a sequence comprising at least five amino acids encoded within the CA7 CG04 locus.

The present invention further provides methods of screening the CA7 CG04 gene to identify mutations. Such methods may further comprise the step of amplifying a portion of the CA7 CG04 locus, and may further include a step of providing a set of polynucleotides which are primers for amplification of said portion of the CA7 CG04 locus. Such methods may also include a step of providing the complete set of short polynucleotides defined by the sequence of CA7 CG04 or discrete subsets of that sequence, all single-base substitutions of that sequence or discrete subsets of that sequence, all 1-, 2-, 3-, or 4-base deletions of that sequence or discrete subsets of that sequence, and all 1-, 2-, 3-, or 4-base insertions in that sequence or discrete subsets of that sequence. The method is useful for identifying mutations for use in either diagnosis of the predisposition to cancer or the diagnosis or prognosis of cancer.

The present invention further provides methods of screening suspected CA7 CG04 mutant alleles to identify mutations in the CA7 CG04 gene.

In addition, the present invention provides methods to screen drugs for inhibition of CA7 CG04 gene product function as an anticancer therapy. Since the CA7 CG04 gene is an oncogene which acts as an activator of ras, any small molecule which interrupts this interaction will have anticancer activity. Thus, such drugs are useful for therapy.

It is a discovery of the present invention that the CA7 CG04 locus which predisposes individuals to prostate cancer, is a gene encoding an CA7 CG04 protein, which has been found to have no significant homology with publicly available protein or DNA sequences. This gene is termed CA7 CG04 herein. It is a discovery of the present invention that mutations in the CA7 CG04 locus in the germline are indicative of a predisposition to prostate cancer. It is a further discovery that mutations in the CA7 CG04 gene segregates with prostate cancer, breast cancer, cervical cancer and others. It is a discovery of the present invention that somatic mutations in the CA7 CG04 locus are also associated with prostate and other types of cancer. Finally, it is a discovery of the present invention that two common missense mutations of CA7 CG04 are associated with both prostate and many other types of cancer. The mutational events of the CA7 CG04 locus can involve deletions, insertions and point mutations within the coding sequence and the non-coding sequence. The preliminary evidence is that CA7 CG04 is an oncogene.

STRATEGY FOR THE MOLECULAR CLONING OF CA7 CG04

Starting from the HPC1 region on chromosome 1 of the human genome, a region which contains a genetic locus, CA7 CG04, which causes susceptibility to cancer, including prostate cancer, has been identified.

The region containing the CA7 CG04 locus was identified using a variety of genetic techniques. Genetic mapping techniques initially defined the CA7 CG04 region in terms of recombination with genetic markers. Based upon studies of large extended families ("kindreds") with multiple cases of prostate cancer, a chromosomal region has been pinpointed that contains the CA7 CG04 gene, as well as putative susceptibility alleles in the CA7 CG04 locus.

Population Resources

Large, well-documented Utah kindreds are especially important in providing good resources for human genetic studies. Each large kindred independently gives evidence whether or not a CA7 CG04 predisposing allele is segregating in that family. Recombinants informative for localization and isolation of the CA7 CG04 locus could be obtained only from kindreds large enough to confirm the presence of a susceptibility allele. Large sibships are especially important for studying prostate cancer, since penetrance of the CA7 CG04 predisposing allele is reduced both by age and sex, making informative sibships difficult to find. Furthermore, large sibships are essential for constructing haplotypes of deceased individuals by inference from the haplotypes of their close relatives.

Genetic Mapping

Given a set of informative families, genetic markers are essential for linking a disease to a region of a chromosome. Such markers include restriction fragment length polymorphisms (RFLPs) (Botstein et al., 1980), markers with a variable number of tandem repeats (VNTRs) (Jeffreys et al., 1985; Nakamura et al., 1987), and an abundant class of DNA polymorphisms based on short tandem repeats (STRs), especially repeats of CpA (Weber and May, 1989; Litt et al., 1989). To generate a genetic map, one selects potential genetic markers and tests them using DNA extracted from members of the kindreds being studied.

Genetic markers useful in searching for a genetic locus associated with a disease can be selected on an ad hoc basis, by densely covering a specific chromosome, or by detailed analysis of a specific region of a chromosome. A preferred method for selecting genetic markers linked with a disease involves evaluating the degree of informativeness of kindreds to determine the ideal distance between genetic markers of a given degree of polymorphism, then selecting markers from known genetic maps which are ideally spaced for maximal efficiency. Informativeness of kindreds is measured by the probability that the markers will be heterozygous in unrelated individuals. It is also most efficient to use STR markers which are detected by amplification of the target nucleic acid sequence using PCR; such markers are highly informative, easy to assay (Weber and May, 1989), and can be assayed simultaneously using multiplexing strategies (Skolnick and Wallace, 1988), greatly reducing the number of experiments required.

Once linkage has been established, one needs to find markers that flank the disease locus, i.e., one or more markers proximal to the disease locus, and one or more markers distal to the disease locus. Where possible, candidate markers can be selected from a known genetic map. Where none is known, new markers can be identified by the STR technique.

Contig assembly

Given a genetically defined interval flanked by meiotic recombinants, one needs to generate a contig of genomic clones that spans that interval. Publicly available resources, such as the Whitehead integrated maps of the human genome (e.g., the WICGR Chr 1 map of Nov. 19, 1996) provide aligned chromosome maps of genetic markers, other sequence tagged sites (STSs), radiation hybrid map data, and CEPH yeast artificial chromosome (YAC) clones. From the map data, one can often identify a set of yeast artificial chromosomes (YACs) that span the genetically defined interval. Oligonucleotide primer pairs for the markers located in the interval can be synthesized and used to screen libraries of bacterial artificial chromosomes (BACs) and P1 artificial chromosomes (PACs). Successive rounds of BAC/PAC library screening with BAC or PAC end markers enables the completion of a BAC/PAC clone contig that spans the genetically defined interval.

Genomic sequencing

Given a tiling path of BAC and PAC clones across a defined interval, one useful gene finding strategy is to generate an almost complete genomic sequence of that interval. Random genomic clone sublibraries can be prepared from each BAC or PAC clone in the tiling path. Individual sublibrary clones sufficient in number to generate an, on average, 6x redundant sequence of each BAC or PAC can then be end-sequenced with vector primers. These sequences can be assembled into sequence contigs, and these contigs placed in a local genomic sequence database. One can search the genomic sequence contigs for sequence similarity with known genes and expressed sequence tags (ESTs), examine them for the presence of long open translational reading frames, and characterize them for CpG dinucleotide frequency.

Hybrid selection

Given a tiling path of BAC and PAC clones across a defined interval, another useful gene finding strategy is to obtain cDNA clones cognate to the tiling path BACs and PACs. One preferred cDNA cloning strategy is hybrid selection. cDNA can be prepared from a number of human tissues and human cell lines in such a manner that the cDNA molecules have PCR primer binding sites (anchors) at each end. This cDNA can be affinity captured with the tiling path BACs and PACs. Captured cDNA can then be PCR amplified using the anchor primers and then cloned. Individual clones can then be end-sequenced with vector primers. The sequences of these cDNA clones can be analyzed for similarity to genomic sequence contigs generated from BACs and PACs on the tiling path. One can then identify individual exons of genes in the genetically defined interval by parsing the sequences of true-positive hybrid selected clones across these genomic sequence contigs.

RACE and inter-exon PCR

While hybrid selection is an efficient approach to the initial identification of novel genes located within a defined interval of the genome, the approach is not often the most efficient way to complete the cloning of those genes. Rapid amplification of cDNA ends (RACE) provides a PCR based method to identify new 5' and 3' cDNA sequences. cDNA can be prepared from a number of human tissues in a manner such that the cDNA molecules have PCR primer binding sites (anchors) at their 5' ends, 3' ends, or both. PCR amplification from this cDNA with 5' end anchor primers and gene specific reverse primers can generate 5' RACE products. Similarly, PCR amplification with 3' end anchor primers and gene specific forward primers can generate 3' RACE products. cDNA cloning techniques can also miss exons that lie between already known exons of a gene; for instance, this can easily occur if a particular exon is only included in a relatively rare splice variant of a transcript. Combinatorial inter-exon PCR is an effective strategy for detecting these exons. One can design a forward primer based on sequences from the first known exon of the gene and a set of reverse primers, one based on the sequence of each of the downstream exons (or any subset thereof) of the gene. Then one can PCR amplify from cDNA of tissues and cell lines thought to express the gene, using all the combinations of the forward primer with each reverse primer. Combinations as complex as a forward primer from each exon paired with a reverse primer from each exon, subject only to the limitation that the forward primer should be from an exon upstream of the exon from which the reverse primer was designed, can be tried. PCR products which differ in length from the expected product can be gel purified. In either RACE or combinatorial inter-exon PCRs, the PCR products can either be gel purified and then sequenced directly or first cloned and then sequenced.

cDNA library screening

Another useful strategy for finding new 5', 3', or internal sequences is cDNA library screening. One can make or purchase bacteriophage 1 cDNA libraries prepared from RNA from tissues or cell lines thought to express the gene. One then screens plaque lifts from those libraries with labeled nucleic acid probes based on the currently known sequences of the gene of interest. Individual positive clones are purified, and then the clone inserts can be sequenced.

Mutation screening

Proof that any particular gene located within the genetically defined interval is CA7 CG04 is obtained by finding sequences in DNA or RNA extracted from affected kindred members which create abnormal CA7 CG04 gene products or abnormal levels of CA7 CG04 gene product. Such CA7 CG04 predisposing alleles will co-segregate with the disease in large kindreds. They will also be present at a much higher frequency in non-kindred individuals with prostate cancer than in individuals in the general population. Finally, since tumors often mutate somatically at loci which are in other instances mutated in the germline, we expect to see normal germline CA7 CG04 alleles mutated into sequences which are identical or similar to CA7 CG04 predisposing alleles in DNA extracted from tumor tissue. Whether one is comparing CA7 CG04 sequences from tumor tissue to CA7 CG04 alleles from the germline of the same individuals, or one is comparing germline CA7 CG04 alleles from cancer cases to those from unaffected individuals, the key is to find mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary, tertiary or quaternary protein structure. Small deletions or base pair substitutions could also significantly alter protein expression by changing the level of transcription, splice pattern, mRNA stability, or translation efficiency of the CA7 CG04 transcript. Silent mutations or those resulting in conservative amino acid substitutions would not generally be expected to disrupt protein function.

Useful Diagnostic Techniques

According to the diagnostic and prognostic method of the present invention, alteration of the wild-type CA7 CG04 locus is detected. In addition, the method can be performed by detecting the wild-type CA7 CG04 locus and confirming the lack of a predisposition to cancer at the CA7 CG04 locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. The finding of CA7 CG04 mutations thus provides diagnostic information. A CA7 CG04 allele which is not deleted (e.g., found on the sister chromosome to a chromosome carrying an CA7 CG04 deletion) can be screened for other mutations, such as insertions, small deletions, and point mutations. Point mutational events may occur in regulatory regions, such as in the promoter of the gene, or in intron regions or at intron/exon junctions.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful is the recently developed technique of DNA microchip technology.

Predisposition to cancers, such as prostate cancer, and the other cancers identified herein, can be ascertained by testing any tissue of a human for mutations of the CA7 CG04 gene. For example, a person who has inherited a germline CA7 CG04 mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the CA7 CG04 gene. Alteration of a wild-type CA7 CG04 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. For a gene as large as CA47 CG04, manual sequencing is very labor-intensive, but under optimal conditions, mutations in the coding sequence of a gene are rarely missed. Another approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation.

In order to detect the alteration of the wild-type CA7 CG04 gene in a tissue, it is helpful to isolate the tissue free from surrounding normal tissues. Means for enriching tissue preparation for tumor cells are known in the art. For example, the tissue may be isolated from paraffin or cryostat sections. Cancer cells may also be separated from normal cells by flow cytometry. These techniques, as well as other techniques for separating tumor cells from normal cells, are well known in the art. If the tumor tissue is highly contaminated with normal cells, detection of mutations is more difficult.

Detection of point mutations may be accomplished by molecular cloning of the CA7 CG04 allele(s) and sequencing the allele(s) using techniques well known in the art. Alternatively, the gene sequences can be amplified directly from a genomic DNA preparation from the tumor tissue, using known techniques. The DNA sequence of the amplified sequences can then be determined.

There are six well known methods for a more complete, yet still indirect, test for confirming the presence of a susceptibility allele: 1) single-stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Rano and Kidd, 1989). For allele-specific PCR, primers are used which hybridize at their 3' ends to a particular CA7 CG04 mutation. If the particular CA7 CG04 mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the CA7 CG04 mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its MRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type CA7 CG04 gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the CA7 CG04 mRNA or gene but can be a segment of either. If the riboprobe comprises only a segment of the CA7 CG04 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the CA7 CG04 gene can also be detected using Southern hybridization, especially if the changes are gross rearrangements, such as deletions and insertions.

DNA sequences of the CA7 CG04 gene which have been amplified by use of PCR may also be screened using allele-specific probes. These probes are nucleic acid oligomers, each of which contains a region of the CA7 CG04 gene sequence harboring a known mutation. For example, one oligomer may be about 30 nucleotides in length (although shorter and longer oligomers are also usable as well recognized by those of skill in the art), corresponding to a portion of the CA7 CG04 gene sequence. By use of a battery of such allele-specific probes, PCR amplification products can be screened to identify the presence of a previously identified mutation in the CA7 CG04 gene. Hybridization of allele-specific probes with amplified CA7 CG04 sequences can be performed, for example, on a nylon filter. Hybridization to a particular probe under high stringency hybridization conditions indicates the presence of the same mutation in the tumor tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

The most definitive test for mutations in a candidate locus is to directly compare genomic CA7 CG04 sequences from cancer patients with those from a control population. Alternatively, one could sequence messenger RNA after amplification, e.g., by PCR, thereby eliminating the necessity of determining the exon structure of the candidate gene.

Mutations from cancer patients falling outside the coding region of CA7 CG04 can be detected by examining the non-coding regions, such as introns and regulatory sequences near or within the CA7 CG04 gene. An early indication that mutations in noncoding regions are important may come from Northern blot experiments that reveal messenger RNA molecules of abnormal size or abundance in cancer patients as compared to control individuals.

Alteration of CA7 CG04 mRNA expression can be detected by any techniques known in the art. These include Northern blot analysis, PCR amplification and RNase protection. Diminished mRNA expression indicates an alteration of the wild-type CA7 CG04 gene. Alteration of wild-type CA7 CG04 genes can also be detected by screening for alteration of wild-type CA7 CG04 protein. For example, monoclonal antibodies immunoreactive with CA7 CG04 can be used to screen a tissue. Lack of cognate antigen would indicate a CA7 CG04 mutation. Antibodies specific for products of mutant alleles could also be used to detect mutant CA7 CG04 gene product. Such immunological assays can be done in any convenient formats known in the art. These include Western blots, immunohistochemical assays and ELISA assays. Any means for detecting an altered CA7 CG04 protein can be used to detect alteration of wild-type CA7 CG04 genes. Functional assays, such as protein binding determinations, can be used. In addition, assays can be used which detect CA7 CG04 biochemical function. Finding a mutant CA7 CG04 gene product indicates alteration of a wild-type CA7 CG04 gene.

Mutant CA7 CG04 genes or gene products can also be detected in other human body samples, such as serum, stool, urine and sputum. The same techniques discussed above for detection of mutant CA7 CG04 genes or gene products in tissues can be applied to other body samples. Cancer cells are sloughed off from tumors and appear in such body samples. In addition, the CA7 CG04 gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant CA7 CG04 genes or gene products.

The methods of diagnosis of the present invention are applicable to any tumor in which CA7 CG04 has a role in tumorigenesis. The diagnostic method of the present invention is useful for clinicians, so they can decide upon an appropriate course of treatment.

The primer pairs of the present invention are useful for determination of the nucleotide sequence of a particular CA7 CG04 allele using PCR. The pairs of single-stranded DNA primers can be annealed to sequences within or surrounding the CA7 CG04 gene on chromosome 1 in order to prime amplifying DNA synthesis of the CA7 CG04 gene itself. A complete set of these primers allows synthesis of all of the nucleotides of the CA7 CG04 gene coding sequences, i.e., the exons. The set of primers preferably allows synthesis of both intron and exon sequences. Allele-specific primers can also be used. Such primers anneal only to particular CA7 CG04 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from CA7 CG04 sequences or sequences adjacent to CA7 CG04, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the CA7 CG04 open reading frame shown in SEQ ID NO: 1, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the CA7 CG04 gene or mRNA using other techniques.

It has been discovered that individuals with the wild-type CA7 CG04 gene do not have cancer which results from the CA7 CG04 allele. However, mutations which interfere with the function of the CA7 CG04 protein are involved in the pathogenesis of cancer. Thus, the presence of an altered (or a mutant) CA7 CG04 gene which produces a protein having a loss of function, or altered function, directly correlates to an increased risk of cancer. In order to detect an CA7 CG04 gene mutation, a biological sample is prepared and analyzed for a difference between the sequence of the CA7 CG04 allele being analyzed and the sequence of the wild-type CA7 CG04 allele. Mutant CA7 CG04 alleles can be initially identified by any of the techniques described above. The mutant alleles are then sequenced to identify the specific mutation of the particular mutant allele. Alternatively, mutant CA7 CG04 alleles can be initially identified by identifying mutant (altered) CA7 CG04 proteins, using conventional techniques. The mutant alleles are then sequenced to identify the specific mutation for each allele. The mutations, especially those which lead to an altered function of the CA7 CG04 protein, are then used for the diagnostic methods of the present invention.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA) and nucleic acid sequence based amplification (NASBA). These methods are well known and widely practiced in the art. See, e.g., U.S. Pat. Nos. 4,683,195 and 4,683,202 and Innis et al., 1990 (for PCR); and Wu et al., 1989a (for LCR); U.S. Pat. Nos. 5,270,184 and 5,455,166 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the CA7 CG04 region are preferably complementary to, and hybridize specifically to sequences in the CA7 CG04 region or in regions that flank a target region therein. CA7 CG04 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the CA7 CG04 polypeptides and fragments thereof or to polynucleotide sequences from the CA7 CG04 region, particularly from the CA7 CG04 locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the CA7 CG04 polypeptide or fragment. Monoclonal antibodies may be made by injecting mice with the protein polypeptides, fusion proteins or fragments thereof. Monoclonal antibodies will be screened by ELISA and tested for specific immunoreactivity with CA7 CG04 polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15, between 15 and 40, and greater than 40 bases may also be used. The polynucleotides may be composed of DNA, RNA, or synthetic nucleotide analogs.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

As used herein, the terms "diagnosing" or "prognosing," as used in the context of neoplasia, are used to indicate 1) the classification of lesions as neoplasia, 2) the determination of the severity of the neoplasia, or 3) the monitoring of the disease progression, prior to, during and after treatment.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"CA7 CG04 Allele" refers to normal alleles of the CA7 CG04 locus as well as alleles carrying variations that predispose individuals to develop cancer of many sites including, for example, breast, ovarian, colorectal and prostate cancer. Such predisposing alleles are also called "CA7 CG04 predisposing alleles".

"CA7 CG04 Locus", "CA7 CG04 Gene", "CA7 CG04 Nucleic Acids" or "CA7 CG04 Polynucleotide" each refer to polynucleotides, all of which are in the CA7 CG04 region, that are likely to be expressed in normal tissue, certain alleles of which predispose an individual to develop breast, ovarian, colorectal and prostate cancers. Mutations at the CA7 CG04 locus may be involved in the initiation and/or progression of other types of tumors. The locus is indicated in part by mutations that predispose individuals to develop cancer. These mutations fall within the CA7 CG04 region described infra. The CA7 CG04 locus is intended to include coding sequences, intervening sequences and regulatory elements controlling transcription and/or translation. The CA7 CG04 locus is intended to include all allelic variations of the DNA sequence.

These terms, when applied to a nucleic acid, refer to a nucleic acid which encodes an CA7 CG04 polypeptide, fragment, homolog or variant, including, e.g., protein fusions or deletions. The nucleic acids of the present invention will possess a sequence which is either derived from, or substantially similar to a natural CA7 CG04-encoding gene or one having substantial homology with a natural CA7 CG04-encoding gene or a portion thereof.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the CA7 CG04 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, EDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with an CA7 CG04-encoding sequence.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega Biotec, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

"CA7 CG04 Region" refers to a portion of human chromosome 1 containing the CA7 CG04 gene.

As used herein, the terms "CA7 CG04 locus", "CA7 CG04 allele" and "CA7 CG04 region" all refer to the double-stranded DNA comprising the locus, allele, or region, as well as either of the single-stranded DNAs comprising the locus, allele or region.

As used herein, a "portion" of the CA7 CG04 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from any of SEQ ID NOs: 1 and 3–21 and any combination of these sequences as described in further detail below, its complement or functionally equivalent nucleic acid sequences. The present invention does not include nucleic acids which exist in the prior art. That is, the present invention includes all nucleic acids having at least 8 nucleotides derived from any of SEQ ID NOs:1 and 3–21 and any combination of these sequences as described in further detail below with the proviso that it does not include nucleic acids existing in the prior art.

"CA7 CG04 protein" or "CA7 CG04 polypeptide" refers to a protein or polypeptide encoded by the CA7 CG04 locus, variants or fragments thereof. The term "polypeptide" refers to a polymer of amino acids and its equivalent and does not refer to a specific length of the product; thus, peptides, oligopeptides and proteins are included within the definition of a poly-peptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native CA7 CG04 sequence, preferably in excess of about 90%, and more preferably at least about 95% homologous. Also included are proteins encoded by DNA which hybridize under high or low stringency conditions, to CA7 CG04-encoding nucleic acids and closely related polypeptides or proteins retrieved by antisera to the CA7 CG04 protein(s).

An CA7 CG04 polypeptide may be that derived from any of the exons described herein which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of an CA7 CG04 polypeptide. Such polypeptides may have an amino acid sequence which differs from that derived form any of the exons described herein by one or more of addition, substitution, deletion or insertion of one or more amino acids. Preferred such polypeptides have CA7 CG04 function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with an CA7 CG04 polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of an CA7 CG04 polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of a natural CA7 CG04 polypeptide.

"Probes". Polynucleotide polymorphisms associated with CA7 CG04 alleles which predispose to certain cancers or are associated with most cancers are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of a CA7 CG04 predisposing allele.

Probes for CA47 CG04 alleles may be derived from the sequences of the CA47 CG04 region or its cDNAs. The probes may be of any suitable length, which span all or a portion of the CA47 CG04 region, and which allow specific hybridization to the CA47 CG04 region. If the target sequence contains a sequence identical to that of the probe, the probes may be short, e.g., in the range of about 8–30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding CA7 CG04 are preferred as probes. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding CA7 CG04 is present in a cell or tissue. The present invention includes all novel probes having at least 8 nucleotides derived from any of SEQ ID NOs:1 and 3–21 and any combination of these sequences as described in further detail below, its complement or functionally equivalent nucleic acid sequences. The present invention does not include probes which exist in the prior art. That is, the present invention includes all probes having at least 8 nucleotides derived from any of SEQ ID NOs:1 and 3–21 and any combination of these sequences as described in further detail below with the proviso that they do not include probes existing in the prior art.

Similar considerations and nucleotide lengths are also applicable to primers which may be used for the amplification of all or part of the CA7 CG04 gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding CA7 CG04 is present in a cell or tissue. The present invention includes all novel primers having at least 8 nucleotides derived from the CA7 CG04 locus for amplifying the CA7 CG04 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for CA7 CG04 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of CA7 CG04 polypeptides. Immunological activities include both immunogenic function in a target immune system, as well as sharing of immunological epitopes for binding, serving as either a competitor or substitute antigen for an epitope of the CA7 CG04 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for CA7 CG04 polypeptides or fragments thereof is described below.

The present invention also provides for fusion polypeptides, comprising CA7 CG04 polypeptides and fragments. Homologous polypeptides may be fusions between two or more CA7 CG04 polypeptide sequences or between the sequences of CA7 CG04 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial b-galactosidase, trpE, protein A, b-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the CA7 CG04 polypeptides from other biological material, such as from cells transformed with recombinant nucleic acids encoding CA7 CG04, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A CA7 CG04 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases. The % identity is calculated over the entire length of the polypeptide with the largest match between the sequences.

Identity means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Methods commonly employed to determine identity between two sequences include, but are not limited to those disclosed in *Guide to Huge Computers*, Martin J. Bishop, ed., Academic Press, San Diego, 1994, and Carillo, H., and Lipman, D. (1988). Preferred methods to determine identity are designed to give the largest match between the two sequences tested. Such methods are codified in computer programs. Preferred computer program methods to determine identity between two sequences include, but are not limited to, GCG program package (Devereux et al. (1984), BLASTP, BLASTN, FASTA (Altschul et al. (1990); Altschul et al. (1997)).

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30 C, typically in excess of 37 C., and preferably in excess of 45 C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity. The % identity is calculated over the entire length of the polypeptide with the largest match between the sequences.

Homology, for polypeptides, is typically measured using sequence analysis software as described above, including, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type CA7 CG04 nucleic acid or wild-type CA7 CG04 polypeptide. The modified polypeptide will be substantially homologous to the wild-type CA7 CG04 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified poly-peptide may be substantially the same as the activity of the wild-type CA7 CG04 polypeptide. Alternatively, the similarity of function (activity) of the modified polypeptide may be higher than the activity of the wild-type CA7 CG04 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type CA7 CG04 gene function produces the modified protein described above.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

Preparation of Recombinant or Chemically Synthesized Nucleic Acids, Vectors, Tansformation and Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention is described, e.g., in Sambrook et al., 1989 or Ausubel et al., 1992.

The polynucleotides of the present invention may also be produced by chemical synthesis, e.g., by the phosphoramidite method described by Beaucage and Carruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native CA7 CG04 protein or from other receptors or from secreted polypeptides of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al., 1989 or Ausubel et al. 1992.

An appropriate promoter and other necessary vector sequences will be selected so as to be functional in the host, and may include, when appropriate, those naturally associated with CA7 CG04 genes. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England BioLabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Moloney leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. Nos. 5,691,198; 5,735,500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the CA7 CG04 nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan, 1979. Examples of commonly used mammalian host cell lines are VERO and HeLa cells, Chinese hamster ovary (CHO) cells, and W138, BHK, and COS cell lines. An example of a commonly used insect cell line is SF9. However, it will be appreciated by the skilled practitioner that other cell lines may be appropriate, e.g., to provide higher expression, desirable glycosylation patterns, or other features.

Clones are selected by using markers depending on the mode of the vector construction.

The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of CA7 CG04 polypeptides.

Antisense polynucleotide sequences are useful in preventing or diminishing the expression of the CA7 CG04 locus, as will be appreciated by those skilled in the art. For example, polynucleotide vectors containing all or a portion of the CA7 CG04 locus or other sequences from the CA7 CG04 region (particularly those flanking the CA7 CG04 locus) may be placed under the control of a promoter in an antisense orientation and introduced into a cell. Expression of such an antisense construct within a cell will interfere with CA7 CG04 transcription and/or translation and/or replication.

The probes and primers based on the CA7 CG04 gene sequences disclosed herein are used to identify homologous CA7 CG04 gene sequences and proteins in other species. These CA7 CG04 gene sequences and proteins are used in the diagnostic/prognostic, therapeutic and drug screening methods described herein for the species from which they have been isolated.

Methods of Use: Nucleic Acid Diagnosis and Diagnostic Kits

In order to detect the presence of an CA7 CG04 allele predisposing an individual to cancer, a biological sample such as blood is prepared and analyzed for the presence or absence of predisposing alleles of CA7 CG04. In order to detect the presence of neoplasia, the progression toward malignancy of a precursor lesion, or as a prognostic indicator, a biological sample of the lesion is prepared and analyzed for the presence or absence of mutant alleles of CA7 CG04. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant CA7 CG04 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 1. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mittlin, 1989; U.S. Pat. No. 4,868,105, and in EPO Publication No. 225,807.

As noted above, non-PCR based screening assays are also contemplated in this invention.

This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding CA7 CG04. Allele specific probes are also contemplated within the scope of this example and exemplary allele specific probes include probes encompassing the predisposing or potentially predisposing mutations summarized in herein.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting CA7 CG04. Thus, in one example to detect the presence of CA7 CG04 in a cell sample, more than one probe complementary to CA7 CG04 is employed and in particular the number of different probes is alternatively 2, 3, or 5 different nucleic acid probe sequences. In another example, to detect the presence of mutations in the CA7 CG04 gene sequence in a patient, more than one probe complementary to CA7 CG04 is employed where the cocktail includes probes capable of binding to the allele-specific mutations identified in populations of patients with alterations in CA7 CG04. In this embodiment, any number of probes can be used, and will preferably include probes corresponding to the major gene mutations identified as predisposing an individual to prostate cancer. Some candidate probes contemplated within the scope of the invention include probes that include the allele-specific mutations identified herein and those that have the CA7 CG04 regions corresponding to SEQ ID NOs:1 and 3–21 both 5' and 3' to the mutation site.

Methods of Use: Peptide Diagnosis and Diagnostic Kits

The neoplastic condition of lesions can also be detected on the basis of the alteration of wild-type CA7 CG04 polypeptide. Such alterations can be determined by sequence analysis in accordance with conventional techniques. More preferably, antibodies (polyclonal or monoclonal) are used to detect differences in, or the absence of, CA7 CG04 peptides. The antibodies may be prepared as discussed above under the heading "Antibodies" and as further shown in Examples 12 and 13. Other techniques for raising and purifying antibodies are well known in the art and any such techniques may be chosen to achieve the preparations claimed in this invention. In a preferred embodiment of the invention, antibodies will immunoprecipitate CA7 CG04 proteins from solution as well as react with CA7 CG04 protein on Western or immunoblots of polyacrylamide gels. In another preferred embodiment, antibodies will detect CA7 CG04 proteins in paraffin or frozen tissue sections, using immunocytochemical techniques.

Preferred embodiments relating to methods for detecting CA7 CG04 or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al in U.S. Pat. Nos. 4,376,110 and 4,486,530, hereby incorporated by reference, and exemplified in Example 15.

Methods of Use: Drug Screening

This invention is particularly useful for screening compounds by using a wild-type or mutant CA7 CG04 polypeptide or binding fragment thereof in any of a variety of drug screening techniques.

The CA7 CG04 polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an CA7 CG04 polypeptide or fragment and the agent being tested, or examine the degree to which the formation of a complex between an CA7 CG04 polypeptide or fragment and a known ligand, e.g. ras, is interfered with by the agent being tested.

Thus, the present invention provides methods of screening for drugs comprising contacting such an agent with an CA7 CG04 polypeptide or fragment thereof and assaying (i) for the presence of a complex between the agent and the CA7 CG04 polypeptide or fragment, or (ii) for the presence of a complex between the CA7 CG04 polypeptide or fragment and a ligand, by methods well known in the art. In such competitive binding assays the CA7 CG04 polypeptide or fragment is typically labeled. Free CA7 CG04 polypeptide or fragment is separated from that present in a protein:protein complex, and the amount of free (i.e., uncomplexed) label is a measure of the binding of the agent being tested to CA7 CG04 or its interference with CA7 CG04:ligand binding, respectively. Since CA7 CG04 is a GEF protein and activates ras, the effect of a drug candidate can be determined by measuring ras activation by a wild-type or mutant CA7 CG04 polypeptide. Peptide ligands which interact with CA7 CG04 are readily identified by a yeast or mammalian two-hybrid assay.

Another technique for drug screening provides high throughput screening for compounds having suitable binding affinity to the CA7 CG04 polypeptides and is described in detail in Geysen, PCT published application WO 84/03564. Briefly stated, large numbers of different small peptide test compounds are synthesized on a solid substrate, such as plastic pins or some other surface. The peptide test compounds are reacted with CA7 CG04 polypeptide and washed. Bound CA7 CG04 polypeptide is then detected by methods well known in the art.

Purified CA7 CG04 can be coated directly onto plates for use in the aforementioned drug screening techniques. However, non-neutralizing antibodies to the polypeptide can be used to capture antibodies to immobilize the CA7 CG04 polypeptide on the solid phase.

This invention also contemplates the use of competitive drug screening assays in which neutralizing antibodies capable of specifically binding the CA7 CG04 polypeptide compete with a test compound for binding to the CA7 CG04 polypeptide or fragments thereof. In this manner, the antibodies can be used to detect the presence of any peptide which shares one or more antigenic determinants of the CA7 CG04 polypeptide.

A further technique for drug screening involves the use of host eukaryotic cell lines or cells (such as described above)

which have a wild-type or mutant CA7 CG04 gene. The host cell lines or cells are grown in the presence of drug compound. The ras activation occurring in the host cells is measured to determine if the compound is capable of regulating the interaction of CA7 CG04 and ras.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an CA7 CG04 specific binding partner, or to find mimetics of an CA7 CG04 polypeptide.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., CA7 CG04 polypeptide) or, for example, of the CA7 CG04-receptor or ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., CA7 CG04 polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved CA7 CG04 polypeptide activity or stability or which act as inhibitors, agonists, antagonists, etc. of CA7 CG04 polypeptide activity. By virtue of the availability of cloned CA7 CG04 sequences, sufficient amounts of the CA7 CG04 polypeptide may be made available to perform such analytical studies as x-ray crystallography. In addition, the knowledge of the CA7 CG04 protein sequence provided herein will guide those employing computer modeling techniques in place of, or in addition to x-ray crystallography.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment of prostate cancer, use of such a substance in the manufacture of a composition for administration, e.g., for treatment of prostate cancer, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

Methods of Use: Antisensense Therapy

The present invention contemplates an antisense polynucleotide up to about 50 nucleotides in length that hybridizes with mRNA molecules that encode a CA7 CG04 polypeptide, and the use of one or more of those polynucleotides in treating cancer cells. See U.S. Pat. Nos. 5,891,858 and 5,885,970, incorporated herein by reference, for further details. The antisense polynucleotide is useful for treating cancer caused by a mutant CA7 CG04 as well as overexpression of a wild-type CA7 CG04.

In one embodiment an antisense polynucleotide is contacted with a cancer cells. The contact is carried out in vivo in a host mammal, and contact is effected by administration to the mammal of a pharmaceutical composition containing the polynucleotide dissolved or dispersed in a physiologically tolerable diluent so that a body fluid such as blood or lymph provides at least a portion of the aqueous medium. In vivo contact is maintained until the polynucleotide is eliminated from the mammal's body by a normal bodily function such as excretion in the urine or feces or enzymatic breakdown.

The polynucleotide may be injected directly into the tumor in an aqueous medium (an aqueous composition) via a needle or other injecting means and the composition is injected throughout the tumor as compared to being injected in a bolus. For example, an aqueous composition containing an antisense polynucleotide, the inverts or mixtures thereof is injected into tumors via a needle. The needle is placed in the tumors and withdrawn while expressing the aqueous composition within the tumor. That mode of administration is carried out in three approximately orthogonal planes in the tumors.

This administration technique has the advantages of delivering the polynucleotide directly to the site of action and avoids most of the usual body mechanisms for clearing drugs. Tumors such as prostate tumors can frequently be located by palpation so that exact placement of the polynucleotide can be carried out. In addition, modern imaging techniques such as X-ray, ultrasound and MRI can be used to locate the tumors for treatment where palpation may be insufficient to locate a tumor.

A polynucleotide can also be administered in the form of liposomes. As is shown in the art, liposomes are generally derived from phospholipids or other lipid substances. Liposomes are formed by monoor multi-lamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are phospholipids and phosphatidyl cholines (lecithins), both natural and synthetic.

An antisense polynucleotide can also be administered by gene therapy. The polynucleotide may be introduced into the cell in a vector such that the polynucleotide remains extrachromosomal. In such a situation, the polynucleotide will be expressed by the cell from the extrachromosomal location. Vectors for introduction of polyucleotides for extrachromosomal maintenance are known in the art, and any suitable vector may be used. Methods for introducing DNA into cells such as electroporation, calcium phosphate coprecipitation and viral transduction are known in the art, and the choice of method is within the competence of the routineer.

The antisense polynucleotide, may be employed in gene therapy methods in order to decrease the amount of the expression products of CA7 CG04 in cancer cells, especially in those cases where CA7 CG04 is overexpressed. Such gene therapy is particularly appropriate for use in both cancerous and pre-cancerous cells. It may also be useful to decrease the level of expression of CA7 CG04 even in those tumor cells in which a wild-type gene is expressed at an elevated level.

Gene therapy would be carried out according to generally accepted methods, for example, as described in further detail in U.S. Pat. No. 5,747,282 and references cited therein, all incorporated by reference herein. Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences conventionally used.

Gene transfer techniques which target DNA directly to, e.g. prostate tissues, e.g., epithelial cells of the prostate, are preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

Methods of Use: Nucleic Acid Based Therapies

According to the present invention, a method is also provided of supplying wild-type CA7 CG04 function to a cell which carries mutant CA7 CG04 alleles. The wild-type CA7 CG04 gene or a part of the gene may be introduced into the cell in a vector such that the gene remains extrachromosomal. In such a situation, the gene will be expressed by the cell from the extrachromosomal location. If a gene fragment is introduced and expressed in a cell carrying a mutant CA7 CG04 allele, the gene fragment should encode a part of the CA7 CG04 protein which is required for normal physiological processes of the cell. More preferred is the situation where the wild-type CA7 CG04 gene or a part thereof is introduced into the mutant cell in such a way that it recombines with the endogenous mutant CA7 CG04 gene present in the cell. Such recombination requires a double recombination event which results in the correction of the CA7 CG04 gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of the routineer. See also U.S. Patent Nos. 5,800,998 and 5,891,628, each incorporated by reference herein.

Among the compounds which may exhibit anti-cancer activity are antisense, ribozyme, and triple helix molecules. Such molecules may be designed to reduce or inhibit mutant CA7 CG04 activity. Techniques for the production and use of such molecules are well known to those of skill in the art, such as described herein or in U.S. Pat. No. 5,800,998, incorporated herein by reference.

Antisense RNA and DNA molecules act to directly block the translation of mRNA by binding to targeted mRNA and preventing protein translation. With respect to antisense DNA, oligodeoxyribonucleotides derived from the translation initiation site, e.g., between the −10 and +10 regions of the CA7 CG04 nucleotide sequence of interest, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. The composition of ribozyme molecules must include one or more sequences complementary to the target CA7 CG04 mRNA, preferably the mutant CA7 CG04 mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding CA7 CG04, preferably mutant CA7 CG04 proteins.

Specific ribozyme cleavage sites within any potential RNA target are initially identified by scanning the target molecule for ribozyme cleavage sites which include the following sequence: GUA, GUU and GUC. Once identified, short RNA sequences of between 15 and ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays.

Nucleic acid molecules to be used in triplex helix formation should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC.sup.+triplets across the three associated strands of the resulting triple helix. The pyrimidine-rich molecules provide base complementarity to a purine-rich region of a single strand of the duplex in a parallel orientation to that strand. In addition, nucleic acid molrcules may be chosen that are purine-rich, for example, contain a stretch of guanidine residues. These molecules will 'form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'–3', 3'–5' manner, such that they base pair with one strand of a duplex first and then the other, eliminating the necessity for a sizeable stretch of either purines or pyrimidines to be present on one strand of a duplex.

It is possible that the antisense, ribozyme, and/or triple helix molecules described herein may reduce or inhibit the translation of mRNA produced by both normal and mutant CA7 CG04 alleles. In order to ensure that substantial normal levels of CA7 CG04 activity are maintained in the cell, nucleic acid molecules that encode and express CA7 CG04 polypeptides exhibiting normal CA7 CG04 activity may be introduced into cells which do not contain sequences susceptible to whatever antisense, ribozyme, or triple helix treatments. Such sequences may be introduced via gene therapy methods. Alternatively, it may be preferable to coadminister normal CA7 CG04 protein into the cell or tissue in order to maintain the requisite level of cellular or tissue CA7 CG04 activity. Antisense RNA and DNA molecules, ribozyme molecules and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Gene therapy would be carried out according to generally accepted methods, for example, as described in further detail in U.S. Pat. Nos. 5,837,492 and 5,800,998 and references cited therein, all incorporated by reference herein. Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences conventionally used.

Methods of Use: Peptide Therapy

Peptides which have CA7 CG04 activity can be supplied to cells which carry mutant or missing CA7 CG04 alleles. Peptide therapy is performed as described herein or using well known techniques, such as described in U.S. Pat. Nos. 5,800,998 and 5,891,628, each incorporated herein by reference.

Protein can be produced by expression of the cDNA sequence in bacteria, for example, using known expression vectors. Alternatively, CA7 CG04 polypeptide can be extracted from CA7 CG04-producing mammalian cells. In addition, the techniques of synthetic chemistry can be employed to synthesize CA7 CG04 protein. Any of such techniques can provide the preparation of the present invention which comprises the CA7 CG04 protein. Preparation is substantially free of other human proteins. This is most readily accomplished by synthesis in a microorganism or in vitro.

Active CA7 CG04 molecules can be introduced into cells by microinjection or by use of liposomes, for example. Alternatively, some active molecules may be taken up by cells, actively or by diffusion. Extracellular application of the CA7 CG04 gene product may be sufficient to affect tumor growth. Supply of molecules with CA7 CG04 activity should lead to partial reversal of the neoplastic state. Other molecules with CA7 CG04 activity (for example, peptides, drugs or organic compounds) may also be used to effect such a reversal. Modified polypeptides having substantially similar function are also used for peptide therapy.

Alternatively, antibodies that are both specific for mutant CA7 CG04 gene product and interfere with its activity may be used. Such antibodies may be generated using standard techniques described herein or using conventional techniques, such as described in U.S. Pat. Nos. 5,837,492; 5,800,998 and 5,891,628, against the proteins themselves or against peptides corresponding to the binding domains of the proteins. Such antibodies include but are not limited to polyclonal, monoclonal, Fab fragments, F(ab').sub.2 fragments, single chain antibodies, chimeric antibodies, humanized antibodies etc.

Methods of Use: Transformed Hosts: Transgenic/Knockour Animals and Models

Similarly, cells and animals which carry a mutant CA7 CG04 allele can be used as model systems to study and test for substances which have potential as therapeutic agents. The cells are typically cultured epithelial cells. These may be isolated from individuals with CA7 CG04 mutations, either somatic or germline. Alternatively, the cell line can be engineered to carry the mutation in the CA7 CG04 allele, as described above. After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant CA7 CG04 alleles, usually from a second animal species, as well as insertion of disrupted homologous genes. Alternatively, the endogenous CA7 CG04 gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992) to produce knockout or transplacement animals. A transplacement is similar to a knockout because the endogenous gene is replaced, but in the case of a transplacement the replacement is by another version of the same gene. After test substances have been administered to the animals, the growth of tumors must be assessed. If the test substance prevents or suppresses the growth of tumors, then the test substance is a candidate therapeutic agent for the treatment of the cancers identified herein. These animal models provide an extremely important testing vehicle for potential therapeutic products.

In one embodiment of the invention, transgenic animals are produced which contain a functional transgene encoding a functional CA7 CG04 polypeptide or variants thereof. Transgenic animals expressing CA7 CG04 transgenes, recombinant cell lines derived from such animals and transgenic embryos may be useful in methods for screening for and identifying agents that induce or repress function of CA7 CG04. Transgenic animals of the present invention also can be used as models for studying indications such as cancers.

In one embodiment of the invention, a CA47 CG04 transgene is introduced into a non-human host to produce a transgenic animal expressing a human or murine CA7 CG04 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous CA7 CG04 by homologous recombination between the transgene and the endogenous gene; or the endogenous gene may be eliminated by deletion as in the preparation of "knock-out" animals. Typically, a CA7 CG04 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress CA7 CG04 or express a mutant form of the polypeptide. Alternatively, the absence of a CA7 CG04 in " knock-out" mice permits the study of the effects that loss of CA7 CG04 protein has on a cell in vivo. Knock-out mice also provide a model for the development of CA7 CG04-related cancers.

Methods for producing knockout animals are generally described by Shastry (1995, 1998) and Osterrieder and Wolf (1998). The production of conditional knockout animals, in which the gene is active until knocked out at the desired time is generally described by Feil et al. (1996), Gagneten et al. (1997) and Lobe and Nagy (1998). Each of these references is incorporated herein by reference.

As noted above, transgenic animals and cell lines derived from such animals may find use in certain testing experiments. In this regard, transgenic animals and cell lines capable of expressing wild-type or mutant CA7 CG04 may be exposed to test substances. These test substances can be screened for the ability to reduce overepression of wild-type CA7 CG04 or impair the expression or function of mutant CA7 CG04.

Pharmaceutical Compositions and Routes of Administration

The CA7 CG04 polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); Riott, *Essential Immunology*, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986).

The present invention is described by reference to the following Examples, which are offered by way of illustration and are not intended to limit the invention in any manner. Standard techniques well known in the art or the techniques specifically described below were utilized.

EXAMPLE 1

Ascertain and Study Kindreds Likely to Have a Chromosome 1-Linked Prostate Cancer Susceptibility Locus Extensive cancer prone kindreds were ascertained from a defined population providing a large set of extended kindreds with multiple cases of prostate cancer and many relatives available to study for analysis of candidate genes in the HPC1 region.

Each kindred was extended through all available connecting relatives, and to all informative first degree relatives of each proband or cancer case. For these kindreds, additional prostate cancer cases and individuals with cancer at other sites of interest (e.g., bladder) who also appeared in the kindreds were identified through the tumor registry linked files. All prostate cancers reported in the kindred which were not confirmed in the Utah Cancer Registry were verified. Medical records or death certificates were obtained for confirmation of all cancers. Each key connecting individual and all informative individuals were invited to participate by providing a blood sample from which DNA was extracted. We also sampled spouses, siblings, and offspring of deceased cases so that the genotype of the deceased cases could be inferred from the genotypes of their relatives.

Each of the Utah pedigrees studied represents the descendants of a single founder for whom a significant excess of prostate cancer cases was observed among all descendants. Since all affected descendants are studied, the resulting kindreds represent a collection of both closely and distantly related prostate cancer cases. The criteria for selection of kindreds to analyze for CA7 CG04 linkage were: 1) genotypes available, or inferable, for 6 or more prostate cancer cases, and 2) at least 3 genotyped cases within a second degree of relationship to another genotyped case.

The Utah kindreds are 5–7 generations deep, and contain between 8 and 29 prostate cancer cases. They are all Caucasian of Northern European ancestry. The median age-of-onset for each kindred ranged from 64 to 76, similar to that estimated for the general population. Five percent of cases were diagnosed before age 55. For each kindred analyzed, the number of prostate cancer cases, the median age and range of age-of-onset, and the number of cases and family members sampled and included in this analysis were detailed.

EXAMPLE 2

Selection of Kindreds Which are Linked to Chromosome 1

Nuclear pellets were extracted from 16 ml of ACD blood, and DNA extracted with phenol and chloroform, precipitated with ethanol, and resuspended in Tris-EDTA. The markers used for genotyping were short tandem repeat (STR) loci at 1q24–25 which flanked the most likely HPC1 location as indicated in Smith et al. (1996). The most likely location as suggested in Smith et al. (1996) is at D1S254.

Amplification of 20 ng genomic DNA was performed according to standard PCR procedures, with minor modifications to optimize product clarity, in a total reaction mix of 10 ml. Radiolabeled PCR products were electrophoresed on standard 6% polyacrylamide denaturing sequencing gels. Gels were then dried and autoradiographed. A total of over 200 prostate cancer cases and approximately 800 of their relatives were genotyped for the markers.

In the kindreds which showed evidence of segregation, up to an additional 35 markers were used to identify and confirm segregation of multiple linked markers (haplotypes). Two-point linkage analysis was performed with the package LINKAGE (Lathrop et al., 1984; 1985) using the FASTLINK implementation (Cottingham et al., 1993; Schaffer et al., 1994). The statistical analysis for the inheritance of susceptibility to prostate cancer used the model described in Smith et al. (1996). This model assumed a rare autosomal dominant susceptibility locus and allowed for a 15% sporadic rate of prostate cancer. Marker allele frequencies were estimated from unrelated individuals present in the kindreds.

Linkage in the presence of heterogeneity was assessed by the admixture test (A-test) of Ott (1986). HOMOG, which postulates two family types, linked and unlinked, was used. Multipoint linkage analysis was performed using VITESSE (O'Connell et al., 1995). The size of the pedigrees and the lack of genotyping of the higher generations due to the late age-of-onset, made more-than-three-point analyses impossible.

The two-point Lod scores for the 29 kindreds combined were highly negative at the 3 markers examined, suggesting an overall lack of evidence for this susceptibility locus across all kindreds. Heterogeneity analysis of the three loci showed weak, non-significant evidence for one locus, explaining 5% of the pedigrees. The positive Lod score observed for D1S254 in analysis of heterogeneity, as well as the low estimate of alpha reported in Smith et al. (1996) suggested that there might be a subset of linked pedigrees within our data set. We examined three marker haplotypes in each kindred for evidence of a shared region among affecteds. For those kindreds which suggested such segregation, we genotyped samples for up to an additional markers Multipoint linkage analysis resulted in a maximum heterogeneity Lod score of +1.20 at D1S254 with an estimate that 5% of kindreds were linked. Multipoint heterogeneity analysis in the most likely interval excluded linkage (Lod scores less than −2.00) for alpha greater than 0.33.

Cancers of sites other than prostate would also be expected to occur in individuals in these kindreds. Some individuals hypothesized to be sharing the segregating chromosome 1 haplotype were affected with cancer at another site. Lod scores for linkage for a phenotype of cancer of any site did not differ significantly from those for prostate alone, although most individuals with cancer of another site were not included in the sampling.

EXAMPLE 3

Contig Assembly

Genomic clone contig assembly in the HPC1 region started from a publicly available integrated map of chromosome 1, the WICGR Chr 1 map of Nov. 19, 1996. YACs located in the interval between D1S202 and D1 S238 were ordered from Genome Systems. Primer pairs for the markers located in the interval between D1S202 and D1S238 were synthesized and used to screen a BAC library at Myriad. Markers that were negative on that BAC library were used to screen the BAC and PAC libraries at Genome Systems. DNA preps were prepared from the BACs and PACs that contained these markers. End sequences were obtained by dye terminator sequencing with vector primers on ABI 377 sequencers. Primer pairs defining BAC or PAC end markers were designed from these sequences. These new markers were checked against the YACs to make sure that they mapped within the interval. If the map data were ambiguous, the markers were also checked against a radiation hybrid panel. These new markers were checked against the already identified BACs/PACs to determine the positions of these clones relative to each other. The outside markers from each clone contig were used to screen the Myriad BAC library; those that were negative on that BAC library were used to screen the BAC and PAC libraries at Genome Systems. Repeated cycles of library screening and marker development allowed us to build a BAC/PAC contig that spanned the minimal recombinant interval.

EXAMPLE 4

Genomic Sequencing

Two different types of genomic sequencing sublibraries were prepared from BAC or PAC clones in the candidate region.

Random-Sheared Sequencing Sub-libraries

BAC or PAC DNA was sheared by sonication. To generate blunt-ended fragments, the sonicated DNA was incubated with mung-bean nuclease (Pharmacia Biotech) followed by treatment with a Pfu polishing kit (Stratagene). The DNA fragments were size fractionated on a 0.8% TAE agarose gel, and fragments in the size range of 1.0≠1.6 kb were excised under longwave (365 nm) ultraviolet light. The excised gel slice was rotated 180 degrees relative to the original direction of electrophoresis and then placed into a new gel tray containing 1.0% GTG-Seaplaque low-melting temperature agarose (FMC corporation) before the gel solidified. Electrophoresis was repeated for the same time and voltage as the first run, resulting in a concentration of the DNA fragments in a small volume of agarose, and the gel slice containing the DNA fragments was once again excised from the gel. The DNA fragments were purified from the agarose by incubating the gel slice with beta-agarose (New England Biolabs), followed by removal of the agarose monomers using disposable microconcentrators (Amicon) that employ a 50,000 Daltons molecular weight cutoff filter. DNA fragments were ligated into the Hinc II site of the plasmid pMYG2, a pBluescript (Stratagene) derivative where the polylinker has been replaced by a different polylinker MYG2. The vector was prepared by digestion with Hinc II followed by dephosphorylation with calf alkaline phosphatase (Boehringer Mannheim).

Ligated products were transformed into DH5α $E.$ $coli$ competent cells (Life Technologies, Inc.) and plated on LB plates containing ampicillin, IPTG, and Bluo-gal (Sigma; Life Technologies, Inc.) . White colonies were used to inoculate individual wells of 1 ml 96-well microtiter plates (Beckman) containing 200 microliters of LB media supplemented with ampicillin at 50 micrograms per milliliter. The plates were incubated for 16–20 hours in a shaking incubator at 37 degrees Celsius. After incubation, 20 microliters of dimethyl sulfoxide was added to each well and the plates stored frozen. The inserts of random-sheared clones were amplified from $E.$ $coli$ cultures by PCR with vector primers, and the PCR products were sequenced with M13 forward or reverse fluorescent energy transfer (FET) dye-labeled primers on ABI 377 sequencers.

Sau 3A Sequencing Sub-libraries

BAC or PAC DNA was partially digested with the restriction enzyme Sau 3A, and fragments in the size range of 5–8 kb were size fractionated and recovered from the agarose gel as described above for random-sheared fragments. Sau 3A fragments were ligated into the Bam HI site of pMYG1, a pBluescript (Stratagene) derivative where the polylinker has been replaced by a different polylinker MYGI. The vector was prepared by digestion with Bam HI and dephosphorylation with shrimp alkaline phosphatase (Amersham). The ligated products were transformed and plated as described above for random-sheared clones.

To identify clones containing inserts in the size range of 5–8 kb, bacterial colonies were screened using a plasmid preparation procedure that has been adapted for use in a 96-well format. White colonies were picked into individual wells of 2 ml 96-well plates (Continental Laboratory Products) containing 1 ml LB media supplemented with 200 micrograms per milliliter ampicillin. The plates were incubated 16–20 hours in a shaking incubator at 37 degrees Celsius. A bacterial stock of these clones was prepared by transferring 100 microliters of the 1 ml cultures to another 96-well plate containing 200 microliters of LB media supplemented with ampicillin. The remaining cells were pelleted by centrifugation and the pellets resuspended in 200 microliters of LB media. One hundred microliters of the concentrated cells were transferred to a 96-well thermowell PCR plate (Costar), and the cells were once again pelleted. The pelleted cells were resuspended in lysis buffer [250 mM Tris-HCl, pH 8.0, 50 mM EDTA, pH 8.0, 8% sucrose, 5% Triton X-100, 1 mM tartrazine, and 666 micrograms per milliliter lysozyme], and the plates were covered with thermowell lids (Costar) and incubated in a MJ Research thermocycler for 2 minutes at 100 degrees Celsius followed by 2 minutes at 25 degrees Celsius. Cell debris was pelleted by centrifugation, and 15 microliters of the supernatant containing the plasmid DNA was electrophoresed on a 0.6×TBE 0.8% agarose gel with appropriate supercoiled size standards to estimate the size of each clone.

The bacterial stocks of clones with inserts in the 5–8 kb size range were used to inoculate 3 ml cultures of LB media supplemented with ampicillin, which were incubated overnight in a shaking incubator at 37 degrees Celsius. Plasmid DNA was prepared from these cultures using the Autogen robotic plasmid preparation machine (Integrated Separation Systems). The resulting DNA templates are subjected to DNA sequencing from both ends with M13 forward or reverse fluorescent energy transfer (FET) dye-labeled primers on ABI 377 sequencers.

DNA sequencing gel files were examined for lane tracking accuracy and adjusted where necessary before data extraction. ABI sample files resulting from gel files were converted to the Standard Chromatogram Format (SCF) [Dear and Staden] and trimmed of sequencing vector (pMYG1 or pMYG2). Trimmed sequences were assembled using Acem.bly (Thierry-Mieg et al., 1995; Durbin and Thierry-Mieg, 1991). Contiguous sequence resulting from automatic assembly was screened for residual vector sequence (both sequencing vector and cloning vector) as well as for bacterial contamination using BLAST (Altschul et al., 1990).

Remaining sequences were arranged according to the relative position and orientation of assembled Sau3AI partial digest clone sequence reads as well as sequence similarity to overlapping genomic clones. Repetitive sequence was masked from the sequence contigs using xblast (Claverie and States, 1993). These masked sequences were placed in a Genetic Data Environment (GDE) (Smith et al., 1994) local database for subsequent similarity searches. Similarities among genomic DNA sequences and hybrid-selected cDNA clones as well as GenBank entries—both DNA and protein—were identified using BLAST. DNA sequences were also characterized with respect to short period repeats, CpG content, and long open reading frames.

EXAMPLE 5

Hybrid Selection

Two distinct methods of hybrid selection were used in this work.

Method 1: cDNA preparation and selection. Poly (A) enriched RNA from human mammary gland, prostate, testis, fetal brain, and placenta tissues and from total RNA of the cell line Caco-2 (ATCC HTB 37) were reverse transcribed using the tailed random primer $RXGN_6$ and M-MLV Reverse Transcriptase (Life Technologies, Inc.). First strand cDNA was poly(A) tailed, 2nd strand synthesis was primed with the oligo $RXGT_{12}$, and then the ds cDNA was expanded by amplification with the primer RXG. Hybrid selection was carried out for two consecutive rounds of hybridization to immobilized BAC, PAC or gel purified YAC DNA as described previously. [Parimoo et al., 1991;

Rommens et al., 1994]. Individual gel purified YACs or groups of two to four overlapping BAC and/or PAC clones were used in individual selection experiments. Hybridizing cDNA was collected, passed over a G50 Fine Sephadex column and amplified using tailed primers. The products were then digested with EcoRI, size selected on agarose gels, and ligated into pBluescript (Stratagene) that had been digested with EcoRI and treated with calf alkaline phosphatase (Boehringer Mannheim). Ligation products were transformed into competent DH5α *E. coli* cells (Life Technologies, Inc.).

Characterization of Retrieved cDNAs. 200 to 300 individual colonies from each ligation (from each 250 kbases of genomic DNA) were picked and gridded into microtiter plates for ordering and storage. Cultures were replica transferred onto Hybond N membranes (Amersham) supported by LB agar with ampicillin. Colonies were allowed to propagate and were subsequently lysed with standard procedures. Initial analysis of the cDNA clones involved a prescreen for ribosomal sequences and subsequent cross screenings for detection of overlap and redundancy.

Approximately 10–25% of the clones were eliminated as they hybridized strongly with radiolabeled cDNA obtained from total RNA. Plasmids from 25 to 50 clones from each selection experiment that did not hybridize in prescreening were isolated for further analysis. The retrieved cDNA fragments were verified to originate from individual starting genomic clones by hybridization to restriction digests of DNAs of the starting clones, of a hamster hybrid cell line that contains chromosome 1 as its only human material, and to human genomic DNA. The clones were tentatively assigned into groups based on the overlapping or non-overlapping intervals of the genomic clones.

Method 2: cDNA Preparation. Poly(A) enriched RNA from human mammary gland, fetal brain, lymphocyte, pancreas, prostate, stomach, and thymus were reverse-transcribed using the tailed random primer $XN_{12}$ and Superscript II reverse transcriptase (Gibco BRL). After second strand synthesis and end polishing, the ds cDNA was purified on Sepharose CL-4B columns (Pharmacia). cDNAs were "anchored" by ligation of a double-stranded oligo RP (RP-2 annealed to RL-1) to their 5' ends (5' relative to mRNA) using T4 DNA ligase. Anchored ds cDNA was then repurified on Sepharose CL-4B columns.

Selection was performed by a modified procedure of Lovett et al. (1991). cDNAs from mammary gland, fetal brain, lymphocyte, pancreas, prostate, stomach, and thymus tissues were first expanded by amplification using a nested version of RP, RP.A and XPCR, and purified by fractionation on Sepharose CL-4B. Selection probes were prepared from purified P1s, BACs or PACs by digestion with HinfI and Exonuclease III. The single-stranded probe was photolabelled with photobiotin (Gibco BRL) according to the manufacturer's recommendations. Probe, cDNA and $C_o$t-1 DNA and poly A DNA were hybridized in 2.4M TEA-Cl, 10 mM $NaPO_4$, 1 mM EDTA. Hybridized cDNAs were captured on streptavidin-paramagnetic particles (Dynal), eluted, and reamplified with a further nested version of RP, RP.B and XPCR, and gel purified. The selected, amplified cDNA was hybridized with an additional aliquot of probe, $C_o$t-1 DNA and poly A DNA. Captured and eluted products were amplified again with RP.B and XPCR, size-selected by gel electrophoresis, and cloned into dephosphorylated HincII cut pUC18. Ligation products were transformed into XL2-Blue ultra-competent cells (Stratagene).

Both methods: Insert-containing clones were identified by blue/white selection on Xgal or Bluo-gal plates. Inserts were amplified by colony PCR with vector primers and then sequenced on ABI 377 sequencers. Alignment of these cDNA sequences to corresponding genomic sequences, and parsing of the revealed exons across those genomic sequences, allowed initial characterization of genes located within the region.

EXAMPLE 6

Inter-exon PCR and RACE for the Identification of new exons (5', 3', or internal) in the HPC1 Region Inter-exon PCR: Following sequence analysis of hybrid selected clones that originated from the HPC1 region, several primers were designed to try to amplify HPC1 region products from fetal brain, breast, pancreas, prostate, stomach, and thymus cDNAs. Amplification was by hot start PCR; conditions used were an initial denaturation step at 95° C. for 30 sec followed by a pause at 80° C. while the polymerase/nucleotide mixture was added to the template/primer mixtures. The hot start was followed by 35 cycles of denaturation at 96° C. (4 s), annealing at 60° C. (10 s) and extension at 72° C. (60 s). Parsing of these cDNA sequences across the genomic sequence of the HPC1 region revealed several new exons of candidate genes within the HPC1 region.

5' RACE: The 5' end exons of candidate genes within the HPC1 were identified by a modified RACE protocol called biotin capture 5' RACE (Tavtigian et al., 1996). Poly(A) enriched RNA from prostate was reverse-transcribed using the tailed random primer $XN_{12}$ and Superscript II reverse transcriptase (Gibco BRL). After second strand synthesis and end polishing, the ds cDNA was purified on Sepharose CL-4B columns (Pharmacia). cDNAs were "anchored" by ligation of a double-stranded oligo RP (RP-2 annealed to RL-1) to their 5' ends (5' relative to mRNA) using T4 DNA ligase. Anchored ds cDNA was then repurified on Sepharose CL-4B columns.

The 5' sequences of candidate genes within the HPC1 region were amplified using different primer combinations, and PCR products were fractionated on an agarose gel, gel purified, and captured on streptavidin-paramagnetic particles (Dynal). Reamplifications were performed if necessary using nested primers. These PCR reactions gave several bands on an agarose gel; the PCR products were gel purified and sequenced in the reverse direction with dye terminator chemistry on an ABI 377 sequencer.

3' RACE: The 3' end exons of candidate genes within the HPC1 region was identified by a modified RACE protocol called biotin capture 3' RACE. Poly(A) enriched RNA from prostate was reverse-transcribed using a tailed random primer and Superscript II reverse transcriptase (Life Technologies). The first strand (heteroduplex) cDNA was purified by fractionation on a Sepharose CL-6B column.

The 3' sequence of candidate genes within the HPC1 region was amplified with a biotinylated forward primer and an the anchor primer. PCR products amplified with these primers were fractionated on an agarose gel, gel purified, and captured on streptavidin-paramagnetic particles (Dynal). Captured material was reamplified as necessary using a nested phosphorylated forward primer PF5 and a tailed random primer.

PCR products were gel purified, ligated into the vector pMYG2, and transformed into DH5α cells. Colony PCR products were sequenced using using dye terminator chemistry on an ABI 377 sequencer.

EXAMPLE 7 cDNA Library Screening

Radioactive probes prepared from hybrid selected clones representative of candidate gene transcripts within the HPC1 region were used as probes to screen a total of 5.5×10^6 recombinant phage from a human prostate λgt11 cDNA library (HL1131b, Clontech). Prehybridization and hybridization was performed at 42° C. in 50% formamide, 5×SSPE, 0.1% SDS, 5×Denhardt's mixture, 0.2 mg/ml denatured salmon sperm DNA and 2 mg/ml poly (A). Dextran sulfate (4% v/v) was included in the hybridization solution only. The filters were rinsed in 2×SSC for 10 minutes at room temperature and then rinsed in 2×SSC/0.1% SDS for 30 minutes at 60° C. followed by two washes in 1×SSC/0.1% SDS for 20 minutes each at 60° C. The positive phage were retested for second and third screenings, as required, to obtain purified plaques for sequencing. Inserts were amplified by phage PCR with vector primers and then sequenced using dye terminator chemistry on ABI 377 sequencers.

EXAMPLE 8

Mutation Screening

Both genomic DNA and cDNA were used as templates for mutation screening.

Genomic DNA: Using genomic DNAs from prostate kindred members, prostate cancer affecteds, and tumor cell lines as templates, nested PCR amplifications were performed to generate PCR products of the candidate genes in the HPC1 region that were screened for mutations. One to 10 ng of genomic DNA were subjected to a 23–26 cycle primary amplification, after which the PCR products were diluted 60-fold and reamplified using nested M13-tailed primers for another 20–25 cycles; either TaqPlus (Stratagene) or AmpliTaq Gold (Perkin Elmer) was used in the PCRs. In general, the PCR conditions used were an initial denaturation step at 95° C. for 1 min (TaqPlus) or 10 min (AmpliTaq Gold), followed by cycles of denaturation at 96° C. (12 s), annealing at 55° C. (15 s) and extension at 72° C. (45–60 s). PCR products were sequenced with M13 forward or reverse fluorescent energy transfer (FET) dye-labeled primers on ABI 377 sequencers. Chromatograms were analyzed for the presence of polymorphisms or sequence aberrations in either the Macintosh program Sequencer (Gene Codes) or the Java program Mutscreen (Myriad, proprietary).

cDNA: Total RNA prepared from either tumor cell lines or prostate kindred lymphocytes was treated with DNase I (Boehringer Mannheim) to remove contaminating genomic DNA, and then reverse transcribed to heteroduplex cDNA with a mix of $N_{10}$ random primers and a tailed oligo dT primer, and Superscript II reverse transcriptase (Life Technologies). This cDNA was used as the template for nested PCR amplifications to generate the cDNA PCR products of the candidate genes that were screened for HPC1 mutations. Using the outer primer pair for each amplicon, 10 ng of cDNA were subjected to a 20 cycle primary amplification, after which the PCR products were diluted 100-fold and reamplified using nested M13-tailed primers for another 25–30 cycles. The cDNAs were amplified by hot start PCRs using TaqPlus DNA polymerase (Stratagene). Conditions used were an initial denaturation step at 95° C. for 30 sec followed by a pause at 80° C. while the polymerase/nucleotide mixture was added to the template/primer mixtures. The hot start was followed by cycles of denaturation at 96° C. (4 s), annealing at 55° C. (10 s) and extension at 72° C. (60 s). PCR products were gel purified and then sequenced with M13 forward or reverse fluorescent energy transfer (FET) dye-labeled primers on ABI 377 sequencers. The sequences of these products were analyzed in GDE to determine their exon structure. Chromatograms were analyzed for the presence of polymorphisms or sequence aberrations in either the Macintosh program Sequencher (Gene Codes) or the Java program Mutscreen (Myriad, proprietary).

EXAMPLE 9

Analysis of Mutations

The DNA samples which were screened for mutations were extracted from blood or tumor samples from patients with prostate or ovarian cancer (or known carriers by haplotype analysis) who were participating in research studies on the genetics of prostate cancer. All subjects signed appropriate informed consent.

In studying the several kindreds, two germline mutations were found in a candidate gene identified as CA7 CG04 which were associated with cancer. The cDNA sequence of the CA7 CG04 gene is set forth in SEQ ID NO:1, with the corresponding protein sequence set forth in SEQ ID NO:2. CA7 CG004 is comprised of 19 exons, the sequences of which are set forth in SEQ ID Nos:3–21. The germline mutations found in CA7 CG04 which segregated in families with cancer are:

| A. Kindred A (coded for confidentiality) | | |
|---|---|---|
| LOD Scores | | |
| prostate CA only: | | 0.88 |
| pros + breast + cervical CA: | | 1.5 |
| Variant | | |
| nucleotide variant: | | C 208 T |
| peptide variant: | | P 70 S |
| Diagnoses of affected carriers in this pedigree: | | |
| prostate dx 64 | prostate dx 53 | prostate dx 55 |
| breast dx 74 | prostate dx 89 | cervix uteri dx 39 |
| B. Kindred B (coded for confidentiality) | | |
| LOD Scores | | |
| prostate CA only: | | 0.47 |
| pros + breast + stomach CA: | | 0.60 |
| Variant | | |
| nucleotide variant: | | C 1024 T |
| peptide variant: | | H 342 Y |
| Diagnoses of affected carriers in this pedigree: | | |
| prostate dx 70 | prostate dx 62 | stomach dx 50 |
| breast dx 72 | prostate dx 78 | prostate dx 71 |
| breast dx 65 | prostate dx 71 | prostate dx 68 |
| prostate dx 66 | prostate dx 56 | prostate dx 60 |

EXAMPLE 10

Analysis of the CA7 CG04 Gene

The structure and function of CA7 CG04 gene are determined according to the following methods.

Biological Studies. Mammalian expression vectors containing CA7 CG04 cDNA are constructed and transfected into appropriate prostate carcinoma cells with lesions in the gene. Wild-type CA7 CG04 cDNA as well as altered CA7 CG04 cDNA are utilized. The altered CA7 CG04 cDNA can be obtained from altered CA7 CG04 alleles or produced as described below. Phenotypic reversion in cultures (e.g., cell morphology, doubling time, anchorage-independent growth)

and in animals (e.g., tumorigenicity) is examined. The studies will employ both wild-type and mutant forms of the gene.

Molecular Genetics Studies. In vitro mutagenesis is performed to construct deletion mutants and missense mutants (by single base-pair substitutions in individual codons and alanine scanning mutagenesis). The mutants are used in biological, biochemical and biophysical studies.

Mechanism Studies. The ability of CA7 CG04 protein to bind to known and unknown DNA sequences is examined. Its ability to transactivate promoters is analyzed by transient reporter expression systems in mammalian cells. Conventional procedures such as particle-capture and yeast two-hybrid system are used to discover and identify any functional partners. The nature and functions of the partners are characterized. These partners in turn are targets for drug discovery.

Structural Studies. Recombinant proteins are produced in E. coli, yeast, insect and/or mammalian cells and are used in crystallographical and NMR studies. Molecular modeling of the proteins is also employed. These studies facilitate structure-driven drug design.

As noted above, CA7 CG04 shares domain(s) in common with guansosine exchange factor (GEF) proteins. Preliminary studies have confirmed that CA7 CG04 is a ras activator.

EXAMPLE 11

Generation of Polyclonal Antibody against CA7 CG04

Segments of CA7 CG04 coding sequence are expressed as fusion protein in E. coli. The overexpressed proteins are purified by gel elution and used to immunize rabbits and mice using a procedure similar to the one described by Harlow and Lane, 1988. This procedure has been shown to generate Abs against various other proteins (for example, see Kraemer, et al., 1993).

Briefly, a stretch of CA7 CG04 coding sequence was cloned as a fusion protein in plasmid PET5A (Novagen, Inc., Madison, Wis.). After induction with IPTG, the overexpression of a fusion protein with the expected molecular weight is verified by SDS/PAGE. Fusion proteins are purified from the gel by electroelution. The identification of the protein as the CA7 CG04 fusion product is verified by protein sequencing at the N-terminus. Next, the purified protein is used as immunogen in rabbits. Rabbits are immunized with 100 mg of the protein in complete Freund's adjuvant and boosted twice in 3 week intervals, first with 100 mg of immunogen in incomplete Freund's adjuvant followed by 100 mg of immunogen in PBS. Antibody containing serum is collected two weeks thereafter.

This procedure can be repeated to generate antibodies against mutant forms of the CA7 CG04 protein. These antibodies, in conjunction with antibodies to wild type CA7 CG04, are used to detect the presence and the relative level of the mutant forms in various tissues and biological fluids.

EXAMPLE 12

Generation of Monoclonal Antibodies Specific for CA7 CG04

Monoclonal antibodies are generated according to the following protocol. Mice are immunized with immunogen comprising intact CA7 CG04 or CA7 CG04 peptides (wild type or mutant) conjugated to keyhole limpet hemocyanin using glutaraldehyde or EDC as is well known.

The immunogen is mixed with an adjuvant. Each mouse receives four injections of 10 to 100 mg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of CA7 CG04 specific antibodies by ELISA or RIA using wild type or mutant CA7 CG04 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 13

Isolation of CA7 CG04 Binding Peptides

Peptides that bind to the CA7 CG04 product are isolated from both chemical and phage-displayed random peptide libraries as follows.

Fragments of the CA7 CG04 gene product are expressed as GST and His-tag fusion proteins in both E. coli and SF9 cells. The fusion protein is isolated using either a glutathione matrix (for GST fusions proteins) or nickel chelation matrix (for His-tag fusion proteins). This target fusion protein preparation is either screened directly as described below, or eluted with glutathione or imidizole. The target protein is immobilized to either a surface such as polystyrene; or a resin such as agarose; or solid supports using either direct absorption, covalent linkage reagents such as glutaraldehyde, or linkage agents such as biotin-avidin.

Two types of random peptide libraries of varying lengths are generated: synthetic peptide libraries that may contain derivatized residues, for example by phosphorylation or myristylation, and phage-displayed peptide libraries which may be phosphorylated. These libraries are incubated with immobilized CA7 CG04 gene product in a variety of physiological buffers. Next, unbound peptides are removed by repeated washes, and bound peptides recovered by a variety of elution reagents such as low or high pH, strong denaturants, glutathione, or imidizole. Recovered synthetic peptide mixtures are sent to commercial services for peptide micro-sequencing to identify enriched residues. Recovered phage are amplified, rescreened, plaque purified, and then sequenced to determined the identity of the displayed peptides.

Use of CA7 CG04 binding peptides

Peptides identified from the above screens are synthesized in larger quantities as biotin conjugates by commercial services. These peptides are used in both solid and solution phase competition assays with CA7 CG04 and its interacting partners identified in yeast 2-hybrid screens. Versions of these peptides that are fused to membrane-permeable motifs (Lin et al., 1995; Rojas et al., 1996) will be chemically synthesized, added to cultured cells and the effects on growth, apoptosis, differentiation, cofactor response, and internal changes will be assayed.

EXAMPLE 14

Sandwich Assay for CA7 CG04

Monoclonal antibody is attached to a solid surface such as a plate, tube, bead, or particle. Preferably, the antibody is attached to the well surface of a 96-well ELISA plate. 100 ml sample (e.g., serum, urine, tissue cytosol) containing the CA7 CG04 peptide/protein (wild-type or mutant) is added to the solid phase antibody. The sample is incubated for 2 hrs at room temperature. Next the sample fluid is decanted, and the solid phase is washed with buffer to remove unbound material. 100 ml of a second monoclonal antibody (to a different determinant on the CA7 CG04 peptide/protein) is added to the solid phase. This antibody is labeled with a detector molecule (e.g., 125-I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of CA7 CG04 peptide/protein present in the sample, is quantitated. Separate assays are performed using monoclonal antibodies which are specific for the wild-type CA7 CG04 as well as monoclonal antibodies specific for each of the mutations identified in CA7 CG04.

EXAMPLE 15

Two-hybrid Assay to Identify Proteins that Interact with CA7 CG04

Sequence encoding all or portions of CA7 CG04 are ligated to pAS2-1 (Clontech) such that the coding sequence of CA7 CG04 is in-frame with coding sequence for the GAL4p DNA-binding domain. This plasmid construct is introduced into the yeast reporter strain Y190 by transformation. A library of activation domain fusion plasmids prepared from human prostate cDNA (Clontech) is then introduced into strain Y190 carrying the pAS2–1-based fusion construct. Transformants are spread onto 20–150 mm plates of yeast minimal media lacking leucine, tryptophan, and histidine, and containing 25 mM 3-amino-1,2,4-triazole. After one week incubation at 30° C., yeast colonies are assayed for expression of the lacZ reporter gene by β-galactosidase filter assay. Colonies that both grow in the absence of histidine and are positive for production of β-galactosidase are chosen for further characterization.

The activation domain plasmid is purified from positive colonies by the smash-and-grab technique. These plasmids are introduced into *E. coli* DH5α by electroporation and purified from *E. coli* by the alkaline lysis method. To test for the specificity of the interaction, specific activation domain plasmids are cotransformed into strain Y190 with plasmids encoding various DNA-binding domain fusion proteins, including fusions to CA7 CG04 and human lamin C. Transformants from these experiments are assayed for expression of the HIS3 and lacZ reporter genes. Positives that express reporter genes with CA7 CG04 constructs and not with lamin C constructs encode bona fide CA7 CG04 interacting proteins. These proteins are identified and characterized by sequence analysis of the insert of the appropriate activation domain plasmid.

This procedure is repeated with mutant forms of the CA7 CG04 gene, to identify proteins that interact with only the mutant protein or to determine whether a mutant form of the CA7 CG04 protein can or cannot interact with a protein known to interact with wild-type CA7 CG04.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Altschul, S. F., et al. (1990). *J. Mol Biol*. 215: 195–197.
Altschul, S. F., et al. (1997). *Nucl. Acids Res*. 25:3389–3402.
Anand, R. (1992). *Techniques for the Analysis of Complex Genomes*, (Academic Press).
Anderson, J. A., et al. (1992). *J. Otolaryngology* 21:321.
Ausubel, F. M., et al. (1992). *Current Protocols in Molecular Biology*, (J. Wiley and Sons, N.Y.).
Bartel, P. L., et al. (1993). "Using the 2-hybrid system to detect protein-protein interactions." In: *Cellular Interactions in Development: A Practical Approach*, Oxford University Press, pp. 153–179.
Beaucage and Carruthers (1981). *Tetra. Letts*. 22:1859–1862.
Botstein, et al. (1980). *Am. J. Hum. Genet*. 32:314–331.
Brinster et al. (1985). *Proc. Natl. Acad Sci. USA* 82:4438–4442.
Cannon, L., et al. (1982). *Cancer Surveys* 1:47–69.
Capecchi, M. R. (1989). *Science* 244:1288.
Cariello (1988). *Human Genetics* 42:726.
Chevray, P. M. and Nathans, D. N. (1992). *Proc. Natl. Acad. Sci. USA* 89:5789–5793.
Claverie, J. M. and States, D. J. (1993). *Computers and Chemistry* 17: 191–201.
Conner, B. J., et al. (1983). *Proc. Natl. Acad. Sci. USA* 80:278–282.
Cotton, et al., (1988). *Proc. Natl Acad. Sci. USA* 85:4397–4401.
Cottingham, R. W., et al. (1993). *Am. J. Hum. Genet*. 53:252–263.
Dear, S. and Staden, R. (1992). *DNA Sequence* 107–110.
Deutscher, M. (1990). *Meth. Enzymology* 182 (Academic Press, San Diego, Calif.).
Donehower, L. A., et al. (1992). *Nature* 356:215.
Durbin, R. and Thierry-Mieg, J. (1991). A *C. elegans* Database. Documentation, code and data available from anonymous FTP servers at lirmm.lirmm.fr, cele.mrc-lmb.cam.ac.uk and ncbi.nlm.nih.gov.
*Enhancers and Eurkaryotic Gene Expression*, Cold Spring Harbor Press, Cold Spring Harbor, N.Y. (1983).
Erickson, J. et al., (1990). *Science* 249:527–533.
Fahy, E., et al al. (1991). *PCR Methods Appl*. 1:25–33.
Fain, P. R. (1992). *Cytogen. Cell Genet*. 60:178.
Feil et al., (1996). *Proc. Natl. Acad. Sci. USA* 93:10887–10890.
Fields, S. and Song, O-K. (1989). *Nature* 340:245–246.
Fiers, et al. (1978). *Nature* 273:113.
Fincham, S. M., et al., Wijayasinghe, C. (1990). *The Prostate* 17:189–206.
Finkelstein, J., et al., (1990). *Genomics* 7:167–172.
Fodor, S. P. A. (1997). DNA Sequencing. Massively Parallel Genomics. *Science* 277:393–395.
Gagneten et al. (1997). *Nucl. Acids Res*. 25:3326–3331.
Glover, D. (1985). *DNA Cloning*, I and II (Oxford Press).
Go, R. C. P., et al. (1983). *J. Natl. Cancer Inst*. 71:455–461.
Goding (1986). *Monoclonal Antibodies: Principles and Practice*, 2d ed. (Academic Press, N.Y.).
Godowski, et al. (1988). *Science* 241:812–816.
Goldgar, D. E., et al. (1994). *J. Natl. Can. Inst*. 86:3:200–209.
Goldgar, D. E., et al (1993). *Am. J. Hum. Genet*. 52:743–748.
Grompe, M., (1993). *Nature Genetics* 5:111–117.
Grompe, M., et al., (1989). *Proc. Natl. Acad. Sci. USA* 86:5855–5892.
Guthrie, G. and Fink, G. R. (1991). *Guide to Yeast Genetics and Molecular Biology* (Academic Press).
Harlow and Lane (1988). *Antibodies: A Laboratory Manual* (Cold Spring Harbor Laboratory, Cold Spring Harbor, N.Y.

Hasty, P., K., et al. (1991). *Nature* 350:243.
Hodgson, J. (1991). *Bio/Technology* 9:19–21.
Hogan et al. (eds) (1994). *Manipulating the Mouse Embryo: A Laboratory Manual*, 2$^{nd}$ Edition, Cold Spring Harbor Laboratory Press, Cold Spring Harbor, N.Y.
Huse, et al. (1989). *Science* 246:1275–1281.
Innis, et al. (1990). *PCR Protocols: A Guide to Methods and Applications* (Academic Press, San Diego, Calif.).
Jablonski, E., et al. (1986). *Nuc. Acids Res.* 14:6115–6128.
Jakoby, W. B. and Pastan, I. H. (eds.) (1979). *Cell Culture. Methods in Enzymology*, Vol. 58 (Academic Press, Inc., Harcourt Brace Jovanovich (N.Y.).
Jeffreys, et al. (1985). *Nature* 314:67–73.
Johnson, et al. (1993). "Peptide Turn Mimetics" In: *Biotechnology and Pharmacy*, Pezzuto et al., eds., Chapman and Hall, N.Y.
Kamb, A. et al. (1994). *Science* 264:436–440.
Kandpal, et al. (1990). *Nucl. Acids Res.* 18:1789–1795.
Kanehisa (1984). *Nucl. Acids Res.* 12:203–213.
Kinszler, K. W., et al. (1991). *Science* 251:1366–1370.
Kinzler, K. W. and Vogelstein, B. 1997. *Nature* 386: 761–763.
Knudson, A. G. (1993). *Nature Genet.* 5:103.
Krain, L. S. (1974). *Preventive Medicine* 3: 154–159.
Kubo, T., et al. (1988). *FEBS Letts.* 241:119.
Kyte, J. and Doolittle, R. F. (1982). *J. Mol. Biol.* 157:105–132.
Landegren, et al. (1988). *Science* 242:229.
Lathrop, G. M., et al. (1985). *Am J. Hum Genet.* 37:482–489.
Lee, J. E., et al. (1995). *Science* 268:836–844.
Lin, Y. Z., et al. (1995). *J. Biol. Chem.* 270:14255–14258.
Litt, et al. (1989). *Am. J. Hum. Genet.* 44:397–401.
Lobe and Nagy (1998). *Bioessays* 20:200–208.
Maniatis. T., et al. (1982). *Molecular Cloning: A Laboratory Manual* (Cold Spring Harbor Laboratory, Cold Spring Harbor, N.Y.).
Martin, R., et al. (1990). *Bio Techniques* 9:762–768.
Matteucci, M. D. and Caruthers, M. H. (1981). *J. Am. Chem. Soc.* 103:3185.
Matthews and Kricka (1988). *Anal. Biochem.* 169:1.
Meikle, A. W., et al. (1985). *Prostate* 6:121.
Merrifield (1963). *J. Am. Chem. Soc.* 85:2149–2156.
Metzger, et al. (1988). *Nature* 334:31–36.
Mittlin (1989). *Clinical Chem.* 35:1819.
Modrich, P. (1991). *Ann. Rev. Genet.* 25:229–253.
Mombaerts, P., et al. (1992). *Cell* 68:869.
Morganti, G., et al. (1956). *Acta Geneticae Medicae et Gemellogogiae* 6:304–305.
Nakamura, et al. (1987). *Science* 235:1616–1622.
Neuhausen, S. L. et al. (1997). *Br. J. Urol.* 79 Suppl. 1:15–20.
Newton, C. R., et al. (1989). *Nucl. Acids Res.* 17:2503–2516.
Nguyen, Q., et al. (1992). *BioTechniques* 13:116–123.
Novack, et al., (1986). *Proc. Natl. Acad. Sci. USA* 83:586.
O'Connell, J. R. and Weeks, D. E. (1995). *Nature Genet.* 11:402–408.
Orita, et al. (1989). *Proc. Natl. Acad. Sci. USA* 86:2776–2770.
Osterrieder and Wolf (1998). *Rev. Sci. Tech.* 17:351–364.
Parimoo, S., et al. (1991). *Proc. Natl. Acad. Sci. USA* 88:9623–9627.
Philpott, K. L., et al. (1992). *Science* 256:1448.
Rano and Kidd (1989). *Nucl. Acids Res.* 17:8392.
Rigby, P. W. J., et al. (1977). *J. Mol. Biol.* 113:237–251.
Rojas, M. Yao, S., and Lin, Y. Z. (1996). *J. Biol. Chem.* 271:27456–27461.
Rommens, J. M., et al. (1994). In: "Identification of transcribed sequences", (U. Hochgeschwender and K. Gardiner, Eds.), pp. 65–79. Plenum Press, N.Y.
Sambrook, J., et al. (1989). *Molecular Cloning A Laboratory Manual*, 2nd Ed. (Cold Spring Harbor Laboratory, Cold Spring Harbor, N.Y.).
Schaffer, A. A., et al. (1994). *Human Heredity* 44:225–237.
Scharf (1986). *Science* 233:1076.
Scopes, R. (1982). *Protein Purification: Principles and Practice*, (Springer-Verlag, N.Y.).
Shastry et al. (1995). *Experientia* 51:1028–1039.
Shastry et al. (1998). *Mol. Cell. Biochem.* 181:163–179.
Sheffield, V. C., et al. (1989). *Proc. Natl. Acad. Sci. USA* 86:232–236.
Sheffield, V. C., et al. (1991). *Am. J. Hum. Genet.* 49:699–706.
Shenk, et al. (1975). *Proc. Natl. Acad. Sci. USA* 72:989.
Shinkai, Y., et al. (1992). *Cell* 68:855.
Skolnick, M. H. and Wallace, B. R. (1988). *Genomics* 2:273–279.
Smith, J. R., et al. (1996). *Science* 274:1371.
Smith, S. A., et al. (1992). *Nature Genetics* 2:128–131.
Smith, S. W., et al. (1994). *CABIOS* 10:671–675.
Smith, T. F. and Waterman, M. S. (1981). *J. Mol. Biol.* 147:195–197.
Snouwaert, J. N., et al. (1992). *Science* 257:1083.
Spargo, C. A., et al. (1996). *Mol. Cell. Probes* 10:247–256.
Tavtigian, S., et al. (1996). *Nature Genetics* 12:333–337.
Thierry-Mieg, D., et al. (1995). Ace.mbly. A graphic interactive program to support shotgun and directed sequencing projects.
Valancius, V. and Smithies, O. (1991). *Mol. Cell Biol.* 11:1402.
Wartell, R. M., et al. (1990). *Nucl. Acids Res.* 18:2699–2705.
Weber and May (1989). *Am. J. Hum. Genet.* 44:388–396.
Wells, J. A. (1991). *Methods in Enzymol.* 202:390–411.
Wetmur and Davidson (1968). *J. Mol. Biol.* 31:349–370.
White, M. B., et al., (1992). *Genomics* 12:301–306.
White and Lalouel (1988). *Ann. Rev. Genet.* 22:259–279.
Woolf, C. M. (1960). *Cancer* 13:739–744.
Wu, et al. (1989a). *Genomics* 4:560–569.

List of Patents and Patent Applications:

U.S. Pat. No. 3,817,837.
U.S. Pat. No. 3,850,752.
U.S. Pat. No. 3,939,350.
U.S. Pat. No. 3,996,345.
U.S. Pat. No. 4,275,149.
U.S. Pat. No. 4,277,437.
U.S. Pat. No. 4,366,241.
U.S. Pat. No. 4,376,110.
U.S. Pat. No. 4,486,530.
U.S. Pat. No. 4,554,101.
U.S. Pat. No. 4,683,195.
U.S. Pat. No. 4,683,202.
U.S. Pat. No. 4,816,567.
U.S. Pat. No. 4,868,105.
U.S. Pat. No. 4,873,191.
U.S. Pat. No. 5,093,246.
U.S. Pat. No. 5,550,050.
U.S. Pat. No. 5,742,282.
U.S. Pat. No. 5,800,998.
U.S. Pat. No. 5,837,492.
U.S. Pat. No. 5,891,628.
U.S. Pat. No. 5,885,970.
U.S. Pat. No. 5,891,858.
Hitzeman et al., EP 73,675A EPO Publication No. 225,807
EP 425,731A.
European Pat. Application Publication No. 0332435
Geysen, H., PCT published application WO 84/03564.
WO 90/07936.
WO 92/19195.
WO 94/25503.
WO 95/01203.
WO 95/05452.
WO 96/02286.
WO 96/02646.
WO 96/11698.
WO 96/40871.
WO 96/40959.
WO 97/12635.

What is claimed is:

1. An isolated nucleic acid coding for a CA7 CG04 polypeptide, said polypeptide having the amino acid sequence set forth in SEQ ID NO:2.

2. The isolated nuicleic acid of claim 1, which comprises the nucleotide sequence set forth in SEQ ID NO:1 or the DNA sequence complementary to the sequence set forth in SEQ ID NO: 1.

3. A vector which comprises the isolated nucleic acid as claimed in claim 1.

4. Host cells transformed and cultured in vitro with the vector claimed in claim 3.

5. An expression vector which comprises the isolated nucleic acid of claim 1, wherein the coding sequence for the CA7 CG04 polypeptide is operably linked to suitable control sequences capable of directing expression of said coding sequence in host cells for said vector.

6. Host cells transformed and cultured in vitro with the vector claimed in claim 5.

7. A method of producing a polypeptide having the amino acid sequence set forth in SEQ ID NO:2 which comprises (i) culturing the host cells of claim 6 containing an expression vector encoding said polypeptide under conditions suitable for the production of said polypeptide and (ii) recovering said polypeptide.

8. The method as claimed in claim 7 which further comprises labeling the recovered polypeptide.

9. The isolated nucleic acid of claim 1 which is an RNA.

10. An isolated nucleic acid coding for a mutated form of the CA7 CG04 polypeptide set forth in SEQ ID NO:2, wherein said mutated form is SEQ ID NO:2 having a mutation selected from the group consisting of a serine at amino acid 70 and a trosine at amino acid 342.

11. The isolated nucleic acid of claim 10 comprising a mutated formn of the nucleotide sequence set forth in SEQ ID NO: 1, wherein said mutated form is SEQ ID NO: 1 having a nucleotide change selected from the group consisting of a C to a T at nucleotide 208 and a C to a T at nucleotide 1024.

12. A DNA wbich is fishy complementary to the nucleic acid of claim 11.

13. A vector which comprises the isolated nucleic acid as claimed in claim 10.

14. Host cells transformed and cultured in vitro with the vector claimed in claim 13.

15. An expressionvectorwhich comprises the isolated nucleic acid of claim 10, wherein the coding sequence for the mutated form of the CA7 CG04 polypeptide is operably linked to suitable control sequences capable of directing expression of said coding sequence in host cells for said vector.

16. Host cells transformed and cultured in vitro with the vector claimed in claim 15.

17. A method of producing a polypeptide having a mutated form of the amino acid sequence set forth in SEQ ID NO:2 which comprises (i) culturing the host cells of claim 16 containing an expression vector encoding said polypeptide under conditions suitable for the production of said polypeptide and (ii) recovering said polypeptide.

18. The isolated nucleic acid of claim 10 which is an RNA.

\* \* \* \* \*

SEQUENCE LISTING

<160> NUMBER OF SEQ ID NOS: 21

<210> SEQ ID NO 1
<211> LENGTH: 2114
<212> TYPE: DNA
<213> ORGANISM: Homo sapiens
<220> FEATURE:
<221> NAME/KEY: CDS
<222> LOCATION: (272)..(1942)
<221> NAME/KEY: misc_feature
<222> LOCATION: (2010)..(2114)
<223> OTHER INFORMATION: n is an unknown nucleotide

<400> SEQUENCE: 1

```
ggtccagctc actctcctcc ccgakcggca gcggcagcgg cggcggcggc ggctgctgcg      60
ggcgctgaat gagagacggt gactgttcgg gtcgacgagt gctactctag gcggcggcgg     120
ccgtggcggt gaagcgtgag gccggcatcg tctttccgtc ctctgaggcg acggccgcgg     180
ctgcacagga ataatgtatt tgtggccttg gacatgaggc agtcagtcct ctgttgctgt     240
taacataagg tcagggactg atgaggaaag c atg gac cta atg aac ggg cag        292
                                   Met Asp Leu Met Asn Gly Gln
                                    1               5 gca agc agt gtc aat att gca gct act gct tct gag aaa agt agc agc        340
Ala Ser Ser Val Asn Ile Ala Ala Thr Ala Ser Glu Lys Ser Ser Ser
            10                  15                  20 tct gaa tcc tta agt gac aaa ggc tct gaa ttg aag aaa agc ttt gat        388
Ser Glu Ser Leu Ser Asp Lys Gly Ser Glu Leu Lys Lys Ser Phe Asp
        25                  30                  35 gct gtg gta ttc gat gtt ctt aag gtt aca cca gaa gaa tat gcg ggt        436
Ala Val Val Phe Asp Val Leu Lys Val Thr Pro Glu Glu Tyr Ala Gly
 40                  45                  50                  55 cag ata aca tta atg gat gtt cca gta ttt aaa gct att caa cca gat        484
Gln Ile Thr Leu Met Asp Val Pro Val Phe Lys Ala Ile Gln Pro Asp
                60                  65                  70 gag ctt tca agt tgt gga tgg aat aaa aaa gaa aaa tat agt tct gca        532
Glu Leu Ser Ser Cys Gly Trp Asn Lys Lys Glu Lys Tyr Ser Ser Ala
            75                  80                  85 cca aat gca gtt gcc ttc aca aga aga ttc aat cat gta agc ttt tgg        580
Pro Asn Ala Val Ala Phe Thr Arg Arg Phe Asn His Val Ser Phe Trp
        90                  95                 100 gtt gtt aga gag att ctt cat gct caa aca tta aaa att aga gca gaa        628
Val Val Arg Glu Ile Leu His Ala Gln Thr Leu Lys Ile Arg Ala Glu
       105                 110                 115 gtt ttg agc cac tat att aaa act gct aag aaa ctg tat gag ctg aat        676
Val Leu Ser His Tyr Ile Lys Thr Ala Lys Lys Leu Tyr Glu Leu Asn
120                 125                 130                 135 aac ctt cat gca ctt atg gca gtg gtt tct ggc cta cag agt gcc cca        724
Asn Leu His Ala Leu Met Ala Val Val Ser Gly Leu Gln Ser Ala Pro
               140                 145                 150 att ttc agg ttg act aaa aca tgg gcg tta tta agt cga aaa gac aaa        772
Ile Phe Arg Leu Thr Lys Thr Trp Ala Leu Leu Ser Arg Lys Asp Lys
```

```
act acc ttt gaa aaa tta gaa tat gta atg agt aaa gaa gat aac tac    820
Thr Thr Phe Glu Lys Leu Glu Tyr Val Met Ser Lys Glu Asp Asn Tyr
        170                 175                 180 aaa aga ctc aga gac tat ata agt agc tta aag atg aca cct tgc att    868
Lys Arg Leu Arg Asp Tyr Ile Ser Ser Leu Lys Met Thr Pro Cys Ile
185                 190                 195 ccc tat tta ggt atc tat ttg tca gat tta aca tac atc gat tca gca    916
Pro Tyr Leu Gly Ile Tyr Leu Ser Asp Leu Thr Tyr Ile Asp Ser Ala
200                 205                 210                 215 tac cca tca act ggc agc att cta gaa aat gag caa aga tca aat tta    964
Tyr Pro Ser Thr Gly Ser Ile Leu Glu Asn Glu Gln Arg Ser Asn Leu
                220                 225                 230 atg aat aat atc ctt cga ata att tct gat tta cag cag tct tgt gaa   1012
Met Asn Asn Ile Leu Arg Ile Ile Ser Asp Leu Gln Gln Ser Cys Glu
                235                 240                 245 tat gat att ccc atg ttg cct cat gtc caa aaa tat ctc aac tct gtt   1060
Tyr Asp Ile Pro Met Leu Pro His Val Gln Lys Tyr Leu Asn Ser Val
        250                 255                 260 cag tat ata gaa gaa cta caa aaa ttt gtg gaa gac gat aat tac aag   1108
Gln Tyr Ile Glu Glu Leu Gln Lys Phe Val Glu Asp Asp Asn Tyr Lys
265                 270                 275 ctt tca tta aag ata gaa cca ggg aca agc acc cca cgt tct gct gct   1156
Leu Ser Leu Lys Ile Glu Pro Gly Thr Ser Thr Pro Arg Ser Ala Ala
280                 285                 290                 295 tcc aga gaa gat tta gta ggt cct gaa gta gga gcg tct cca cag agt   1204
Ser Arg Glu Asp Leu Val Gly Pro Glu Val Gly Ala Ser Pro Gln Ser
                300                 305                 310 gga cga aaa agt gtg gca gct gaa gga gcc ttg ctc cca cag aca ccg   1252
Gly Arg Lys Ser Val Ala Ala Glu Gly Ala Leu Leu Pro Gln Thr Pro
                315                 320                 325 cca tcc cct cgg aat ctg att cca cat gga cat agg aag tgc cat agt   1300
Pro Ser Pro Arg Asn Leu Ile Pro His Gly His Arg Lys Cys His Ser
        330                 335                 340 ttg ggt tat aat ttc att cat aaa atg aac aca gca gaa ttt aag agt   1348
Leu Gly Tyr Asn Phe Ile His Lys Met Asn Thr Ala Glu Phe Lys Ser
345                 350                 355 gca acg ttt cca aat gca gga cca aga cat ctg tta gat gat agc gtc   1396
Ala Thr Phe Pro Asn Ala Gly Pro Arg His Leu Leu Asp Asp Ser Val
360                 365                 370                 375 atg gag ccc cat gcg cca tct cga ggc caa gct gaa agt tct act ctt   1444
Met Glu Pro His Ala Pro Ser Arg Gly Gln Ala Glu Ser Ser Thr Leu
                380                 385                 390 tct agt gga ata tca ata ggt agc agc gat ggt tct gaa cta agt gaa   1492
Ser Ser Gly Ile Ser Ile Gly Ser Ser Asp Gly Ser Glu Leu Ser Glu
                395                 400                 405 gag acc tca tgg cct gct ttt gaa agt tct gca gaa tca gaa gat ttg   1540
Glu Thr Ser Trp Pro Ala Phe Glu Ser Ser Ala Glu Ser Glu Asp Leu
        410                 415                 420 gca gta cat tta tat cca gga gct gtt act att caa ggt gtt ctc agg   1588
Ala Val His Leu Tyr Pro Gly Ala Val Thr Ile Gln Gly Val Leu Arg
425                 430                 435 aga aaa act ttg tta aaa gaa ggc aaa aag cct aca gta gca tct tgg   1636
Arg Lys Thr Leu Leu Lys Glu Gly Lys Lys Pro Thr Val Ala Ser Trp
440                 445                 450                 455 aca aaa tat tgg gca gct ttg tgt ggg aca cag ctt ttt tac tat gct   1684
Thr Lys Tyr Trp Ala Ala Leu Cys Gly Thr Gln Leu Phe Tyr Tyr Ala
                460                 465                 470 gcc aaa tct cta aag gct acc gaa aga aaa cat ttc aaa tca aca tcc   1732
```

```
Ala Lys Ser Leu Lys Ala Thr Glu Arg Lys His Phe Lys Ser Thr Ser
            475                 480                 485 aat aag aac gta tct gtg ata gga tgg atg gtg atg atg gct gat gac      1780
Asn Lys Asn Val Ser Val Ile Gly Trp Met Val Met Met Ala Asp Asp
        490                 495                 500 cct gaa cat cct gat ctc ttc ctg ctg act gac tct gag aaa gga aat      1828
Pro Glu His Pro Asp Leu Phe Leu Leu Thr Asp Ser Glu Lys Gly Asn
505                 510                 515 tcg tac aag ttt caa gct ggc aat aga atg aat gca atg tta tgg ttt      1876
Ser Tyr Lys Phe Gln Ala Gly Asn Arg Met Asn Ala Met Leu Trp Phe
520                 525                 530                 535 aag cat ttg agt gca gcc tgc caa agt aac aaa caa cag gtt cct aca      1924
Lys His Leu Ser Ala Ala Cys Gln Ser Asn Lys Gln Gln Val Pro Thr
                540                 545                 550 aac ttg atg act ttt gag tagaagcctg agaaaaaaag agaggtgaac             1972
Asn Leu Met Thr Phe Glu
                555 tgttgcttct acgtgagcat gaggacctga taaaagagcg ccantattaa tccatcctgc    2032 gcccaaagac atccaccag acctcattat ttcttggctc tattcatttc tgttttcaat     2092 taaaggacat ttgggantaa aa                                             2114

<210> SEQ ID NO 2
<211> LENGTH: 557
<212> TYPE: PRT
<213> ORGANISM: Homo sapiens

<400> SEQUENCE: 2

Met Asp Leu Met Asn Gly Gln Ala Ser Ser Val Asn Ile Ala Ala Thr
1               5                   10                  15

Ala Ser Glu Lys Ser Ser Ser Glu Ser Leu Ser Asp Lys Gly Ser
            20                  25                  30

Glu Leu Lys Lys Ser Phe Asp Ala Val Val Phe Asp Val Leu Lys Val
        35                  40                  45

Thr Pro Glu Glu Tyr Ala Gly Gln Ile Thr Leu Met Asp Val Pro Val
    50                  55                  60

Phe Lys Ala Ile Gln Pro Asp Glu Leu Ser Ser Cys Gly Trp Asn Lys
65                  70                  75                  80

Lys Glu Lys Tyr Ser Ser Ala Pro Asn Ala Val Ala Phe Thr Arg Arg
                85                  90                  95

Phe Asn His Val Ser Phe Trp Val Val Arg Glu Ile Leu His Ala Gln
            100                 105                 110

Thr Leu Lys Ile Arg Ala Glu Val Leu Ser His Tyr Ile Lys Thr Ala
        115                 120                 125

Lys Lys Leu Tyr Glu Leu Asn Asn Leu His Ala Leu Met Ala Val Val
    130                 135                 140

Ser Gly Leu Gln Ser Ala Pro Ile Phe Arg Leu Thr Lys Thr Trp Ala
145                 150                 155                 160

Leu Leu Ser Arg Lys Asp Lys Thr Thr Phe Glu Lys Leu Glu Tyr Val
                165                 170                 175

Met Ser Lys Glu Asp Asn Tyr Lys Arg Leu Arg Asp Tyr Ile Ser Ser
            180                 185                 190

Leu Lys Met Thr Pro Cys Ile Pro Tyr Leu Gly Ile Tyr Leu Ser Asp
        195                 200                 205

Leu Thr Tyr Ile Asp Ser Ala Tyr Pro Ser Thr Gly Ser Ile Leu Glu
    210                 215                 220
```

-continued

| | | | | | | | | | | | |
|---|---|---|---|---|---|---|---|---|---|---|---|
| Asn | Glu | Gln | Arg | Ser | Asn | Leu | Met | Asn | Ile | Leu | Arg | Ile | Ile | Ser |
| 225 | | | | 230 | | | | 235 | | | | 240 |

Asn Glu Gln Arg Ser Asn Leu Met Asn Ile Leu Arg Ile Ile Ser
225                 230                 235                 240

Asp Leu Gln Gln Ser Cys Glu Tyr Asp Ile Pro Met Leu Pro His Val
            245                 250                 255

Gln Lys Tyr Leu Asn Ser Val Gln Tyr Ile Glu Glu Leu Gln Lys Phe
            260                 265                 270

Val Glu Asp Asn Tyr Lys Leu Ser Leu Lys Ile Glu Pro Gly Thr
    275                 280                 285

Ser Thr Pro Arg Ser Ala Ala Ser Arg Glu Asp Leu Val Gly Pro Glu
290                 295                 300

Val Gly Ala Ser Pro Gln Ser Gly Arg Lys Ser Val Ala Ala Glu Gly
305                 310                 315                 320

Ala Leu Leu Pro Gln Thr Pro Pro Ser Pro Arg Asn Leu Ile Pro His
            325                 330                 335

Gly His Arg Lys Cys His Ser Leu Gly Tyr Asn Phe Ile His Lys Met
            340                 345                 350

Asn Thr Ala Glu Phe Lys Ser Ala Thr Phe Pro Asn Ala Gly Pro Arg
            355                 360                 365

His Leu Leu Asp Asp Ser Val Met Glu Pro His Ala Pro Ser Arg Gly
            370                 375                 380

Gln Ala Glu Ser Ser Thr Leu Ser Ser Gly Ile Ser Ile Gly Ser Ser
385                 390                 395                 400

Asp Gly Ser Glu Leu Ser Glu Glu Thr Ser Trp Pro Ala Phe Glu Ser
            405                 410                 415

Ser Ala Glu Ser Glu Asp Leu Ala Val His Leu Tyr Pro Gly Ala Val
            420                 425                 430

Thr Ile Gln Gly Val Leu Arg Arg Lys Thr Leu Leu Lys Glu Gly Lys
            435                 440                 445

Lys Pro Thr Val Ala Ser Trp Thr Lys Tyr Trp Ala Ala Leu Cys Gly
450                 455                 460

Thr Gln Leu Phe Tyr Tyr Ala Ala Lys Ser Leu Lys Ala Thr Glu Arg
465                 470                 475                 480

Lys His Phe Lys Ser Thr Ser Asn Lys Asn Val Ser Val Ile Gly Trp
            485                 490                 495

Met Val Met Met Ala Asp Asp Pro Glu His Pro Asp Leu Phe Leu Leu
            500                 505                 510

Thr Asp Ser Glu Lys Gly Asn Ser Tyr Lys Phe Gln Ala Gly Asn Arg
            515                 520                 525

Met Asn Ala Met Leu Trp Phe Lys His Leu Ser Ala Ala Cys Gln Ser
            530                 535                 540

Asn Lys Gln Gln Val Pro Thr Asn Leu Met Thr Phe Glu
545                 550                 555

<210> SEQ ID NO 3
<211> LENGTH: 189
<212> TYPE: DNA
<213> ORGANISM: Homo sapiens
<220> FEATURE:
<221> NAME/KEY: 5'UTR
<222> LOCATION: (1)..(189)

<400> SEQUENCE: 3
gttccagctc actctcctcc cccgagcggc agcggcagcg gcggcggcgg cggctgctgc     60
gggcgctgaa tgagagacgg tgactgttcg ggtcgacgag tgctactcta ggcggcggcg    120
gccgtggcgg tgaagcgtga ggccggcatc gtctttccgt cctctgaggc gacggccgcg    180

```
gctgcacag                                                              189

<210> SEQ ID NO 4
<211> LENGTH: 140
<212> TYPE: DNA
<213> ORGANISM: Homo sapiens
<220> FEATURE:
<221> NAME/KEY: 5'UTR
<222> LOCATION: (1)..(83)

<400> SEQUENCE: 4
gaataatgta tttgtggcct tggacatgag gcagtcagtc ctctgttgcs ggtaacataa        60
ggtcagggac tgatgaggaa agcatggacc taatgaacgg gcaggcaagc agtgtcaata       120
ttgcagctac tgcttctgag                                                  140

<210> SEQ ID NO 5
<211> LENGTH: 105
<212> TYPE: DNA
<213> ORGANISM: Homo sapiens

<400> SEQUENCE: 5
aaaagtagca gctctgaatc cttaagtgac aaaggctctg aattgaagaa aagctttgat        60
gctgtggtat tcgatgttct taaggttaca ccagaagaat atgcg                      105

<210> SEQ ID NO 6
<211> LENGTH: 51
<212> TYPE: DNA
<213> ORGANISM: Homo sapiens

<400> SEQUENCE: 6
ggtcagataa cattaatgga tgttccagta tttaaagcta ttcaaccaga t                51

<210> SEQ ID NO 7
<211> LENGTH: 84
<212> TYPE: DNA
<213> ORGANISM: Homo sapiens

<400> SEQUENCE: 7
gagctttcaa gttgtggatg gaataaaaaa gaaaaatata gttctgcacc aaatgcagtt        60
gccttcacaa gaagattcaa tcat                                              84

<210> SEQ ID NO 8
<211> LENGTH: 90
<212> TYPE: DNA
<213> ORGANISM: Homo sapiens

<400> SEQUENCE: 8
gtaagctttt gggttgttag agagattctt catgctcaaa cattaaaaat tagagcagaa        60
gttttgagcc actatattaa aactgctaag                                        90

<210> SEQ ID NO 9
<211> LENGTH: 93
<212> TYPE: DNA
<213> ORGANISM: Homo sapiens

<400> SEQUENCE: 9
aaactgtatg agctgaataa ccttcatgca cttatggcag tggtttctgg cctacagagt        60
gccccaattt tcaggttgac taaaacatgg gcg                                    93
```

```
<210> SEQ ID NO 10
<211> LENGTH: 127
<212> TYPE: DNA
<213> ORGANISM: Homo sapiens

<400> SEQUENCE: 10
ttattaagtc gaaaagacaa aactaccttt gaaaaattag aatatgtaat gagtaaagaa      60
gataactaca aaagactcag agactatata agtagcttaa agatgacacc ttgcattccc     120
tatttag                                                              127

<210> SEQ ID NO 11
<211> LENGTH: 138
<212> TYPE: DNA
<213> ORGANISM: Homo sapiens

<400> SEQUENCE: 11
gtatctattt gtcagattta acatacatcg attcagcata cccatcaact ggcagcattc      60
tagaaaatga gcaaagatca aatttaatga ataatatcct tcgaataatt tctgatttac     120
agcagtcttg tgaatatg                                                  138

<210> SEQ ID NO 12
<211> LENGTH: 91
<212> TYPE: DNA
<213> ORGANISM: Homo sapiens

<400> SEQUENCE: 12
atattcccat gttgcctcat gtccaaaaat atctcaactc tgttcagtat atagaagaac      60
tacaaaaatt tgtggaagac gataattaca a                                    91

<210> SEQ ID NO 13
<211> LENGTH: 68
<212> TYPE: DNA
<213> ORGANISM: Homo sapiens

<400> SEQUENCE: 13
gctttcatta aagatagaac cagggacaag cacccacgt tctgctgctt ccagagaaga      60
tttagtag                                                              68

<210> SEQ ID NO 14
<211> LENGTH: 136
<212> TYPE: DNA
<213> ORGANISM: Homo sapiens

<400> SEQUENCE: 14
gtcctgaagt aggagcgtct ccacagagtg gacgaaaaag tgtggcagct gaaggagcct      60
tgctcccaca gacaccgcca tcccctcgga atctgattcc acatggacat aggaagtgcc     120
atagtttggg ttataa                                                    136

<210> SEQ ID NO 15
<211> LENGTH: 152
<212> TYPE: DNA
<213> ORGANISM: Homo sapiens

<400> SEQUENCE: 15
tttcattcat aaaatgaaca cagcagaatt taagagtgca acgtttccaa atgcaggacc      60
aagacatctg ttagatgata gcgtcatgga gccccatgcg ccatctcgag gccaagctga     120
aagttctact ctttctagtg gaatatcaat ag                                  152
```

```
<210> SEQ ID NO 16
<211> LENGTH: 55
<212> TYPE: DNA
<213> ORGANISM: Homo sapiens

<400> SEQUENCE: 16
gtagcagcga tggttctgaa ctaagtgaag agacctcatg gcctgctttt gaaag      55

<210> SEQ ID NO 17
<211> LENGTH: 106
<212> TYPE: DNA
<213> ORGANISM: Homo sapiens

<400> SEQUENCE: 17
ttctgcagaa tcagaagatt tggcagtaca tttatatcca ggagctgtta ctattcaagg   60
tgttctcagg agaaaaactt tgttaaaaga aggcaaaaag cctaca              106

<210> SEQ ID NO 18
<211> LENGTH: 93
<212> TYPE: DNA
<213> ORGANISM: Homo sapiens

<400> SEQUENCE: 18
gtagcatctt ggacaaaata ttgggcagct ttgtgtggga cacagctttt ttactatgct   60
gccaaatctc taaaggctac cgaaagaaaa cat                             93

<210> SEQ ID NO 19
<211> LENGTH: 106
<212> TYPE: DNA
<213> ORGANISM: Homo sapiens

<400> SEQUENCE: 19
ttcaaatcaa catccaataa gaacgtatct gtgataggat ggatggtgat gatggctgat   60
gaccctgaac atcctgatct cttcctgctg actgactctg agaaag             106

<210> SEQ ID NO 20
<211> LENGTH: 92
<212> TYPE: DNA
<213> ORGANISM: Homo sapiens

<400> SEQUENCE: 20
gaaattcgta caagtttcaa gctggcaata gaatgaatgc aatgttatgg tttaagcatt   60
tgagtgcagc ctgccaaagt aacaaacaac ag                             92

<210> SEQ ID NO 21
<211> LENGTH: 74
<212> TYPE: DNA
<213> ORGANISM: Homo sapiens
<220> FEATURE:
<221> NAME/KEY: 3'UTR
<222> LOCATION: (31)..(74)

<400> SEQUENCE: 21
gttcctacaa acttgatgac ttttgagtag aagcctgaga aaaaagaga ggtgaactgt    60 tgcttctacg tgag                                                 74
```